(12) United States Patent
Croce

(10) Patent No.: US 9,297,012 B2
(45) Date of Patent: *Mar. 29, 2016

(54) METHODS AND COMPOSITIONS FOR INDUCING DEREGULATION OF EPHA7 AND ERK PHOSPHORYLATION IN HUMAN ACUTE LEUKEMIAS

(71) Applicant: The Ohio State University Research Foundation, Columbus, OH (US)

(72) Inventor: Carlo M. Croce, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/829,057

(22) Filed: Aug. 18, 2015

(65) Prior Publication Data

US 2015/0344889 A1 Dec. 3, 2015

Related U.S. Application Data

(62) Division of application No. 13/916,699, filed on Jun. 13, 2013, now Pat. No. 9,139,830, which is a division of application No. 12/674,546, filed as application No. PCT/US2008/073964 on Aug. 22, 2008, now Pat. No. 8,466,119.

(60) Provisional application No. 60/965,757, filed on Aug. 22, 2007.

(51) Int. Cl.
| | |
|---|---|
| *C12N 15/11* | (2006.01) |
| *C12N 15/113* | (2010.01) |
| *A61K 31/713* | (2006.01) |
| *A61K 31/7064* | (2006.01) |

(52) U.S. Cl.
CPC ........ *C12N 15/1137* (2013.01); *A61K 31/7064* (2013.01); *A61K 31/713* (2013.01); *C12N 2310/14* (2013.01); *C12N 2320/31* (2013.01)

(58) Field of Classification Search
None
See application file for complete search history.

(56) References Cited

U.S. PATENT DOCUMENTS 6,040,140 A * 3/2000 Croce .................. C07K 14/82
435/6.14

OTHER PUBLICATIONS

Kawagoe et al (Leukemia, 2001, 15: 1743-1749).*
Super et al (Genes, Chromosomes & Cancer, 1997, 20: 185-195).*
Thomas et al (Blood, 2005, 106(10): 3559-3566).*

* cited by examiner

*Primary Examiner* — Sean Aeder
(74) *Attorney, Agent, or Firm* — MacMillan, Sobanski & Todd, LLC

(57) ABSTRACT

Methods for assessing a pathological condition in a subject include measuring one or more markers where a difference is indicative of acute lymphoblastic leukemia (ALL) or a predisposition to ALL, uses and compositions are disclosed.

16 Claims, 9 Drawing Sheets

Figure 1A:
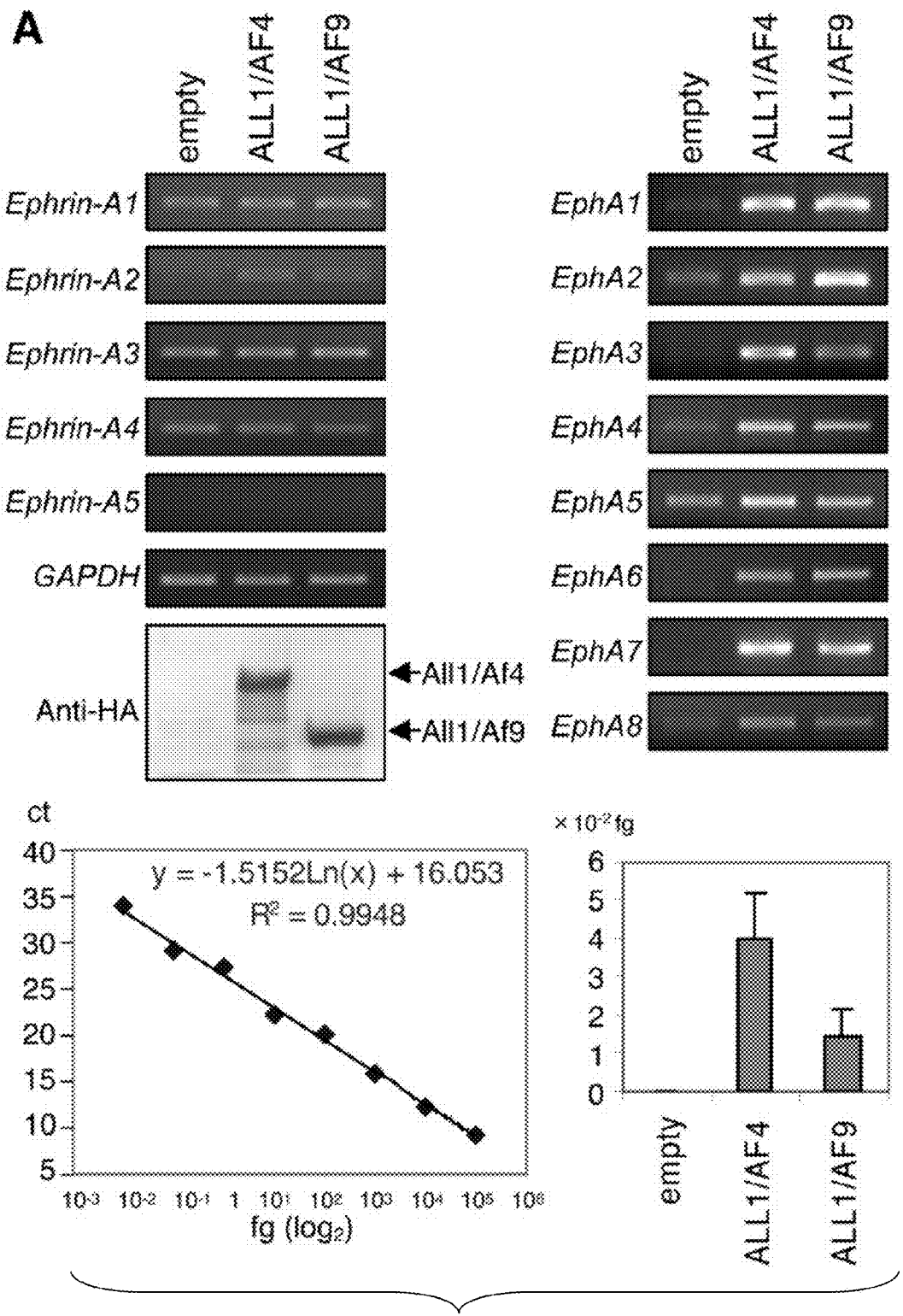

METHODS AND COMPOSITIONS FOR INDUCING DEREGULATION OF EPHA7 AND ERK PHOSPHORYLATION IN HUMAN ACUTE LEUKEMIAS

CROSS-REFERENCE TO RELATED APPLICATIONS

This application is a divisional application of U.S. Ser. No. 13/916,699 filed Jun. 13, 2013, now allowed, which is a divisional application of U.S. Ser. No. 12/674,546 filed Mar. 31, 2010, now U.S. Pat. No. 8,466,119 issued Jun. 18, 2013, which claims the benefit of PCT application No. PCT/US08/073964 filed Aug. 22, 2008 which claims priority to U.S. Provisional Application No. 60/965,757, filed Aug. 22, 2007, the disclosures disclosure of which are is incorporated herein by reference.

STATEMENT REGARDING FEDERALLY SPONSORED RESEARCH

This invention was made with government support under National Institutes of Health Grant No. CA 128609 and US-Israel Binational Grant No. 2003223. The government has certain rights in this invention.

SEQUENCE LISTING

The instant application contains a Sequence Listing which has been submitted in ASCII format via EFS-Web and is hereby incorporated by reference in its entirety. Said ASCII copy, created on Oct. 6, 2008, is named 604_29354_SEQ_LIST_OSURF-08019.txt and is 2 kb in size.

TECHNICAL FIELD AND INDUSTRIAL APPLICABILITY OF THE INVENTION

This invention relates generally to the field of molecular biology. More particularly, it concerns methods and compositions involving biomarkers for human acute leukemias. Certain aspects of the invention include application in diagnostics, therapeutics, and prognostics of human acute leukemias.

BACKGROUND OF THE INVENTION

There is no admission that the background art disclosed in this section legally constitutes prior art.

The ALL1 gene (also termed MLL) has been isolated by virtue of its involvements in recurrent chromosome translocations occurring in acute leukemias, particularly in infant acute lymphoblastic leukemias (ALL) and in therapy-related acute myeloid leukemias (11). The chromosome translocation results in the fusion of the ALL1 gene with one of more than 50 different partner genes and the production of leukemogenic proteins composed of the N-terminal All1 sequence and the C-terminus of the partner protein (11).

The Croce et al. U.S. Pat. No. 5,633,136, which is expressly incorporated herein by reference, discloses that ALL-1 polynucleotides for leukemia detection and treatment. The Croce et al. 136 provides methods for the diagnosis and treatment of human leukemias involving breakpoints on chromosome 11 in the ALL-1 locus. The ALL-1 breakpoint region, an approximately 8 kb region on chromosome 11 is also disclosed. The ALL-1 region is involved in translocations in acute lymphocytic, mylemonocytic, monocytic, and myelogenous leukemias. Probes which identify chromosome aberrations involving the ALL-1 breakpoint region on chromosome 11 are also provided. The cDNA sequence of the ALL-1 gene on chromosome 11 is provided. A partial sequence of the AF-4 gene is also provided in the context of the sequences of the two reciprocal end products of a translocation. Amino acid sequences corresponding to the cDNA sequences of the entire ALL-1 gene and the partial sequence of the AF-4 gene are also provided. Probes are provided for detecting chromosomal abnormalities involving the ALL-1 gene on chromosome 11. Monoclonal antibodies for diagnosis and treatment and antisense oligonucleotides for the treatment of acute leukemias are also described.

The Croce U.S. Pat. No. 5,567,586, which is expressly incorporated herein by reference, discloses methods of indentifying solid tumors with chromosome abnormalities in the ALL-1 region. The Croce '586 provides methods of determining whether a solid tumor has an ALL-1 gene rearrangement or an ALL-1 gene mutation. The methods comprise the steps of obtaining a sample of a solid tumor and detecting the presence of an ALL-1 gene rearrangement or mutation in a cell in said sample. ALL-1 gene rearrangements and mutations are detected by Southern blot analysis, PCR amplification analysis, in situ hybridization analysis, Northern blot analysis or DNA sequence analysis.

The Croce et al. U.S. Pat. No. 5,633,135, which is expressly incorporated herein by reference, discloses chimeric nucleic acids and proteins resulting from ALL-1 region chromosome abnormalities. The Croce et al. '135 provides methods for the diagnosis and treatment of human leukemias involving breakpoints on chromosome 11 in the ALL-1 locus. The ALL-1 breakpoint region, an approximately 8 kb region on chromosome 11, is also disclosed. The ALL-1 region is involved in translocations in acute lymphocytic, myelomonocytic, monocytic and myelogenous leukemias. Probes which identify chromosome aberrations involving the ALL-1 breakpoint region on chromosome 11 are also provided. cDNA sequences of the ALL-1 gene on chromosome 11, the AF-9 gene on chromosome 9 and the AF-4 gene, and corresponding amino acid sequences are also provided. Probes are provided for detecting chromosome abnormalities involving theses genes. Chimeric genes involved in translocations are disclosed. Monoclonal antibodies for diagnosis and treatment and antisense oligonucleotides for treatment of acute leukemias are also described.

The Croce et al. U.S. Pat. No. 6,040,140, which is expressly incorporated herein by reference, describes the cDNA sequence of the ALL-1 gene on chromosome. A partial sequence of the AF-4 gene is also provided in the context of the sequences of two reciprocal endproducts of a translocation. Amino acid sequences corresponding to the cDNA sequences of the entire ALL-1 gene and the partial sequence of the AF-4 gene, and sequences relating to chimeric genes formed by chromosome translocations with chromosome 4, 9 and 19, respectively, are also provided. Probes are also provided for detecting chromosome abnormalities involving the ALL-1 gene on chromosome 11, including probes for detecting chimeric genes generated by translocations.

The most prevalent ALL1 rearrangement in ALL is the ALL1/AF4 chimeric gene resulting from the t(4;11) chromosome translocation. This rearrangement leads to pro-B cell leukemia and is associated with very poor prognosis in infants and adults (12). The molecular pathways deregulated by All1 fusion proteins (14, 21) are only partially defined, but are likely to include process(es) involved in proliferation and differentiation of hematopoietic cells.

In spite of considerable research into therapies, ALL remains difficult to diagnose and treat effectively, and the

SUMMARY OF THE INVENTION

In a first aspect, there is provided herein a method for assessing a pathological condition, or the risk of developing a pathological condition. The method includes measuring an expression profile of one or more markers in a sample from the subject, where a difference in the expression profile in the sample from the subject and an expression profile of a normal sample is indicative of acute lymphoblastic leukemia (ALL) or a predisposition to ALL.

In a particular embodiment, the marker at least comprises one or more gene products that interfere with (Erk) phosphorylation and growth of cells producing ALL/Af4 fusion protein.

In certain embodiments, the assessment of the pathological condition of the subject includes predicting a predisposition to developing ALL in a subject, diagnosing an ALL subject, assessing prognosis of the ALL subject, or assessing response of the ALL subject to therapy.

In certain embodiments, direct EphA7 knockdown or All1/Af4 knockdown-mediated EphA7 suppression in t(4;11) leukemic cells results in attenuation of Erk1/2 phosphorylation.

In another aspect, there is provided herein a marker for predicting survival of a subject with acute lymphoblastic leukemia (ALL) where the marker comprises one or more gene products that interfere with (Erk) phosphorylation and growth of cells producing ALL/Af4 fusion protein.

In another aspect, there is provided herein a method for treatment of leukemic cells carrying the t(4;11) comprising administering an inhibitor of Erk phosphorylation which induces apoptotic cell death.

In another aspect, there is provided herein a method for upregulating EphA7 expression in a subject in need thereon, comprising administering a gene product that codes for All1 fusion proteins that upregulate EphA7 expression.

In another aspect, there is provided herein a marker for assessing one or more metabolic pathways that contribute to at least one of initiation, progression, severity, pathology, aggressiveness, grade, activity, disability, mortality, morbidity, disease sub-classification or other underlying pathogenic or pathological feature of acute lymphoblastic leukemia (ALL), where the marker comprises one or more gene products coding for ALL1 fusion proteins, and wherein the association between the ALL1 fusion proteins and EphA7 expression is highly statistically significant.

In certain embodiments, a level of expression of the marker is assessed by detecting the presence of a transcribed polynucleotide or portion thereof, wherein the transcribed polynucleotide comprises a coding region of the marker.

In another aspect, there is provided herein a composition comprising one or more of the markers as described herein.

In another aspect, there is provided herein a reagent for testing for a cancer-related disease, where the reagent comprises a polynucleotide comprising the nucleotide sequence of at least one marker of claim 7, or a nucleotide sequence complementary to the nucleotide sequence of the marker. In another aspect, the reagent can comprise an antibody that recognizes a protein encoded by at least one marker as described herein.

In another aspect, there is provided herein a method of assessing the effectiveness of a therapy to prevent, diagnose and/or treat acute lymphoblastic leukemia (ALL) comprising: (1) subjecting an animal to a therapy whose effectiveness is being assessed, and (2) determining the level of effectiveness of the treatment being tested in treating or preventing acute lymphoblastic leukemia (ALL) by evaluating at least one marker as described herein.

In certain embodiments, the candidate therapeutic agent comprises one or more of: pharmaceutical compositions, nutraceutical compositions, and homeopathic compositions. In certain embodiments, the therapy being assessed is for use in a human subject.

In another aspect, there is provided herein a pharmaceutical composition for treating acute lymphoblastic leukemia (ALL) cancer, comprising at least one ALL1/Af4 fusion protein expression-inhibition compound, and a pharmaceutically-acceptable carrier. In certain embodiments, the at least one expression-inhibition compound is specific for a gene product that is up- or down-regulated in cancer cells relative to suitable control cells.

In another aspect, there is provided herein an article of manufacture comprising: at least one capture reagent that binds to a marker for a cancer-related disease selected from at least one of the markers as described herein.

In another aspect, there is provided herein a kit for screening for a candidate compound for a therapeutic agent to treat a cancer-related disease, wherein the kit comprises: one or more reagents of at least one marker as described herein, and a cell expressing at least one marker. In certain embodiments, the presence of the marker is detected using a reagent comprising an antibody or an antibody fragment which specifically binds with at least one marker.

In another aspect, there is provided herein a screening test for acute lymphoblastic leukemia (ALL) comprising: contacting one or more of the markers as described herein with a substrate for such marker and with a test agent, and determining whether the test agent modulates the activity of the marker. In certain embodiments, all method steps are performed in vitro.

In another aspect, there is provided herein a method for treating, preventing, reversing or limiting the severity of an acute lymphoblastic leukemia (ALL) complication in an individual in need thereof, comprising: administering to the individual an agent that interferes with an acute lymphoblastic leukemia (ALL) response signaling pathway, in an amount sufficient to interfere with such signaling, where the agent comprises at least one gene product that interferes with (Erk) phosphorylation and growth of cells producing ALL/Af4 fusion protein.

In another aspect, there is provided herein use of an agent that interferes with an acute lymphoblastic leukemia (ALL) response signaling pathway, for the manufacture of a medicament for treating, preventing, reversing or limiting the severity of an acute lymphoblastic leukemia (ALL) complication in an individual. In certain embodiments, the agent comprises at least 5-iodotubericidin (5-ITU).

In another aspect, there is provided herein a method of treating, preventing, reversing or limiting the severity of an acute lymphoblastic leukemia (ALL) complication in an individual in need thereof, comprising administering to the individual an agent that interferes with an acute lymphoblastic leukemia (ALL) disease response cascade. In certain embodiments, the agent comprises 5-iodotubericidin (5-ITU).

In another aspect, there is provided herein use of an agent that interferes with at least an acute lymphoblastic leukemia (ALL) disease response cascade, for the manufacture of a medicament for treating, preventing, reversing or limiting the severity of a cancer-related disease complication in an individual. In certain embodiments, the agent comprises 5-iodotubericidin (5-ITU).

Various objects and advantages of this invention will become apparent to those skilled in the art from the following detailed description of the preferred embodiment, when read in light of the accompanying drawings.

BRIEF DESCRIPTION OF THE FIGURE(S)

Figure 1B:
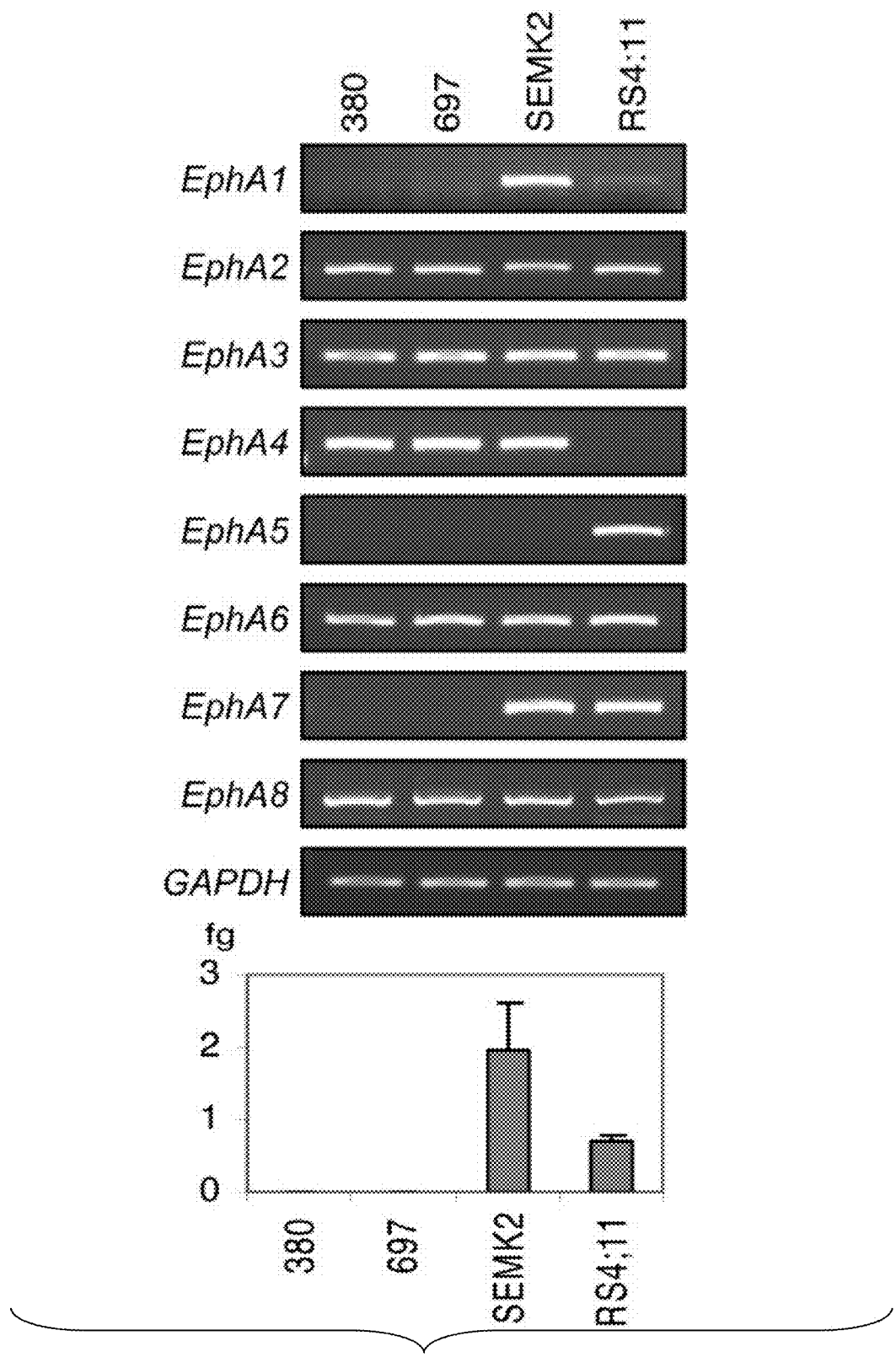

FIGS. 1A and 1B: Detection of EphA/ephrin-A transcripts in K562 cells transfected with ALL1 fusion constructs and in leukemic cell lines with the t(4;11) abnormality:

FIG. 1A: K562 cells transfected with ALL1/AF4 or ALL1/AF9 constructs, pro-B t(4;11) leukemic cell lines SEMK2 and RS4;11, and the pro-B line 380 and pre-B line 697 lacking ALL1 abnormalities were subjected to semi-quantitative RT-PCR analysis to determine the expression level of ephrin-A and/or EphA. "Empty" indicates transfection with vector. Western blot detection of the recombinant All1 fusion proteins with anti-HA mAb in K562 transfectants is shown at the bottom, left.

FIG. 1B: The amounts of EphA7 transcript in the aforementioned cells were quantified by applying real time RT-PCR methodology. cDNAs synthesized from the various cell sources were first determined for their cycle threshold (ct) values for GAPDH. This procedure gave values of 15.01+ 0.11 (mean+SD), indicating similar amounts of total cDNA. The ct values determined for EphA7 were converted to femtogram (fg), according to a standard curve established by using a known amount of EphA7 cDNA (B, left).

Figure 2A:
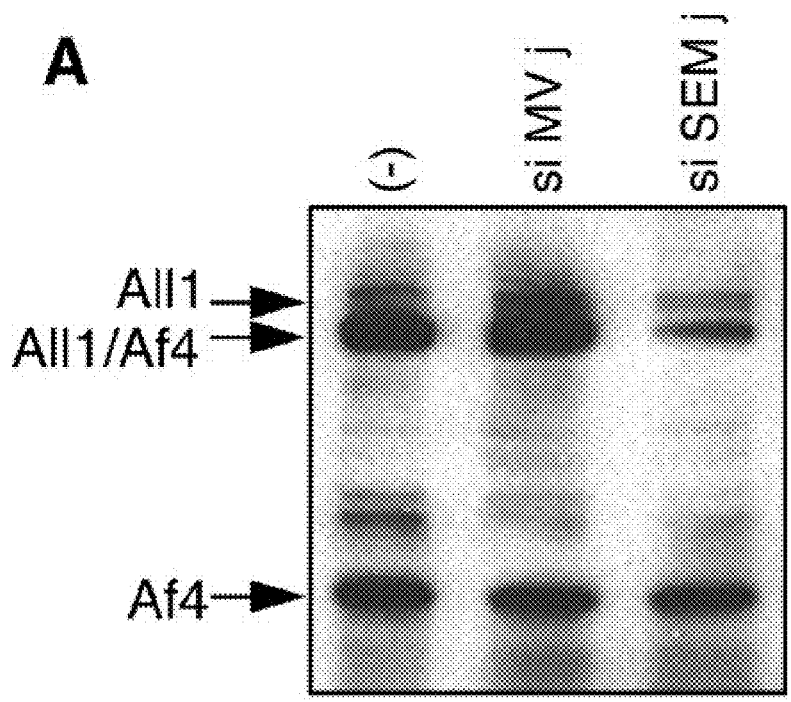
Figure 2B:
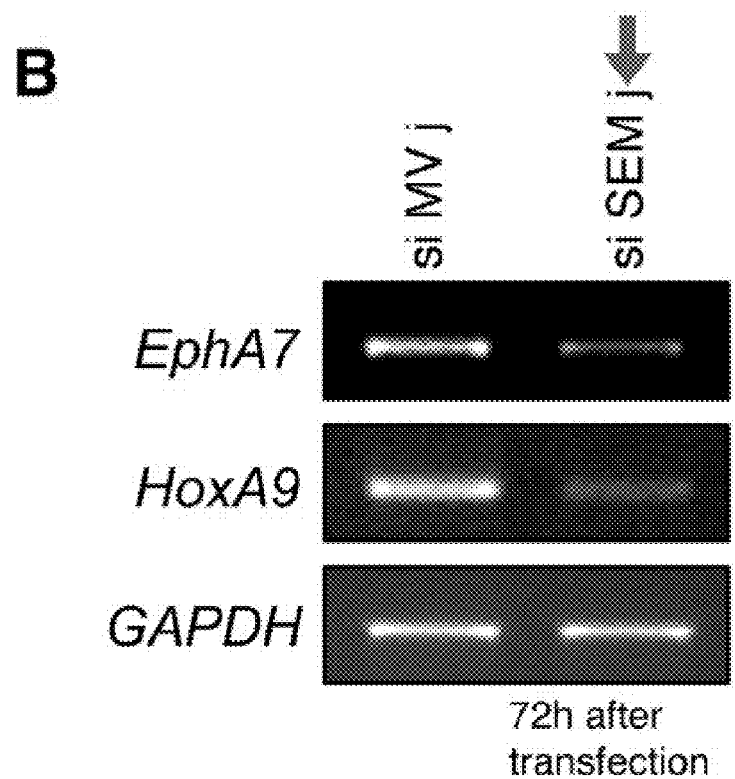

FIGS. 2A and 2B: Suppression of All1/Af4 in SEMK2 cells downregulates EphA7 expression: SEMK2 cells transfected with either junction specific (SEMj) or control (MVj) siRNA were subjected to Western blot analysis for the detection of p300All1 (All1), All1/Af4 and Af4 proteins (FIG. 2A) and to semi-quantitative RT-PCR analysis for the detection of EphA7 and HoxA9 transcripts (FIG. 2B). In A, a mixture of anti-All1 N-terminus and anti-Af4 C-terminus Abs was used as a probe.

Figure 3A:
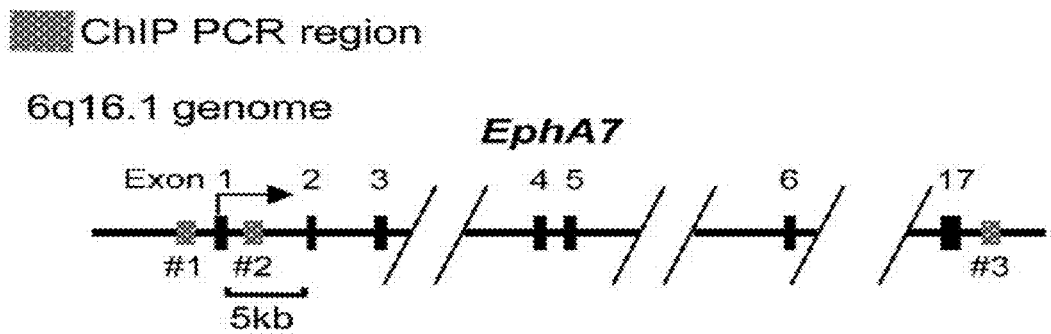
Figure 3B:
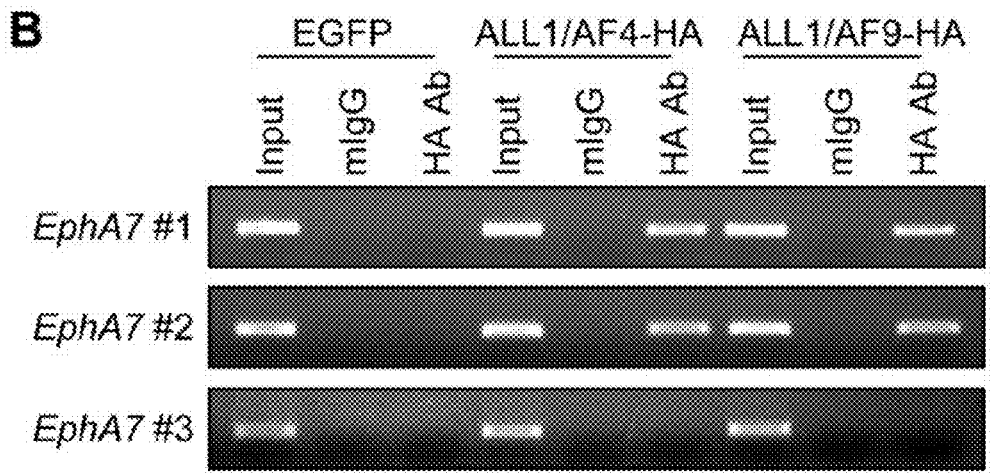
Figure 3C:
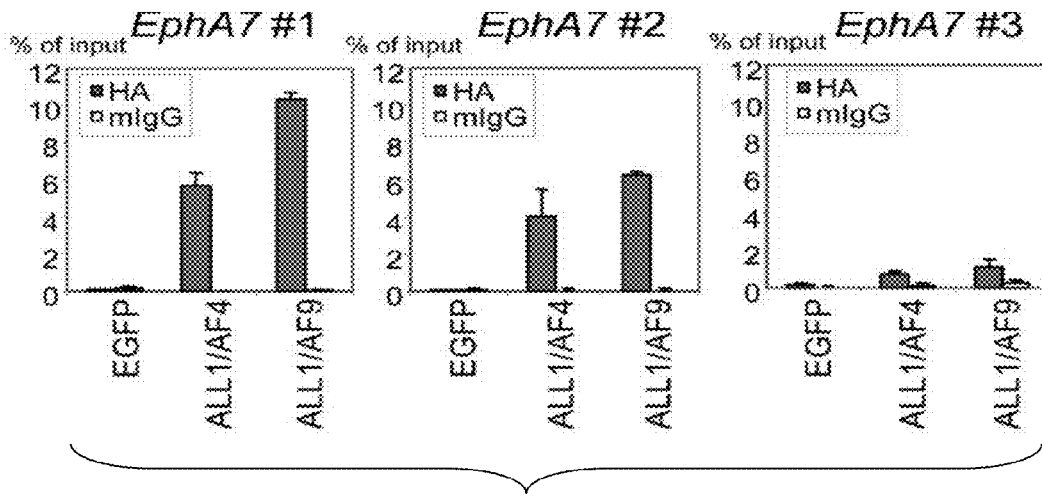

FIGS. 3A-3C: ChIP analysis of the occupancy of All1 fusion proteins on EphA7 genomic regions:

FIG. 3A: Genomic regions within the EphA7 gene, designated #1, 2 and 3, and used for ChIP analysis are shown.

FIG. 3B: ChIP enriched-DNA (using anti-HA mAb) was PCR-amplified and resolved on 2% agarose gel. The EGFP construct in pMACS 4.1 vector was used as a transfection control. mIgG indicates normal mouse IgG used as a control.

FIG. 3C: ChIP-enriched DNA was also subjected to real time PCR analysis. Cycle threshold value determined by using 0.05% of total input set at 100%, and the values determined in the assay using ChIP-enriched DNA are converted to a percentage of the input. Vertical bar in each column indicates standard deviation determined by triplicate assays.

Figure 4A:
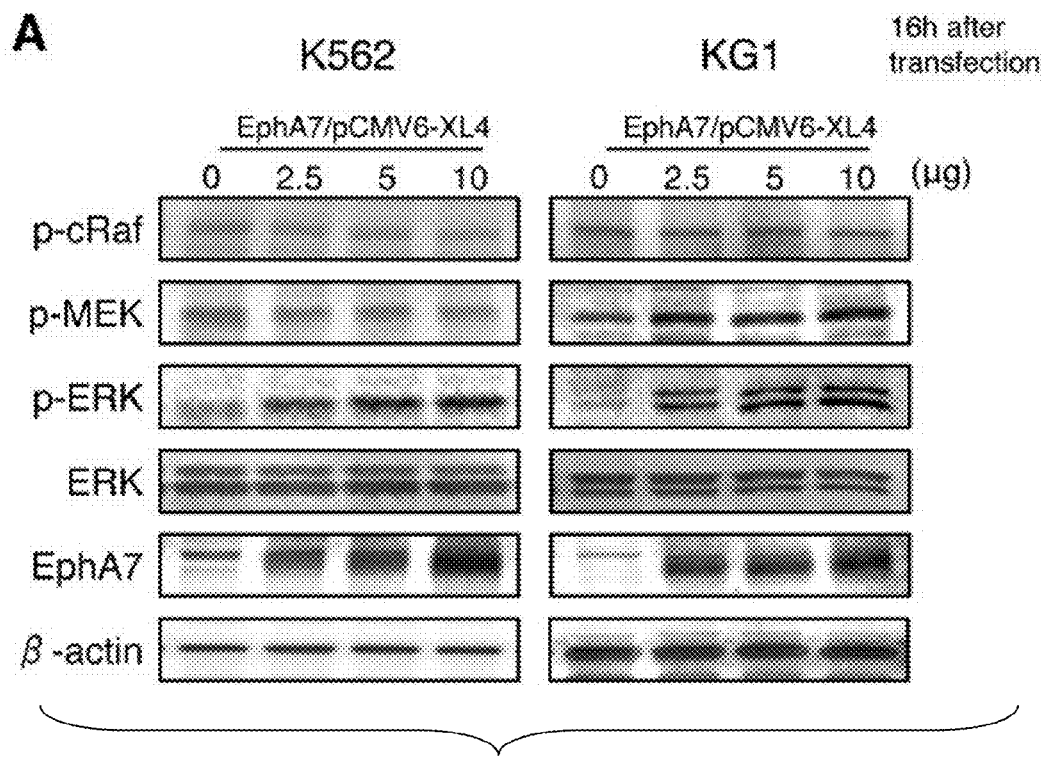
Figure 4B:
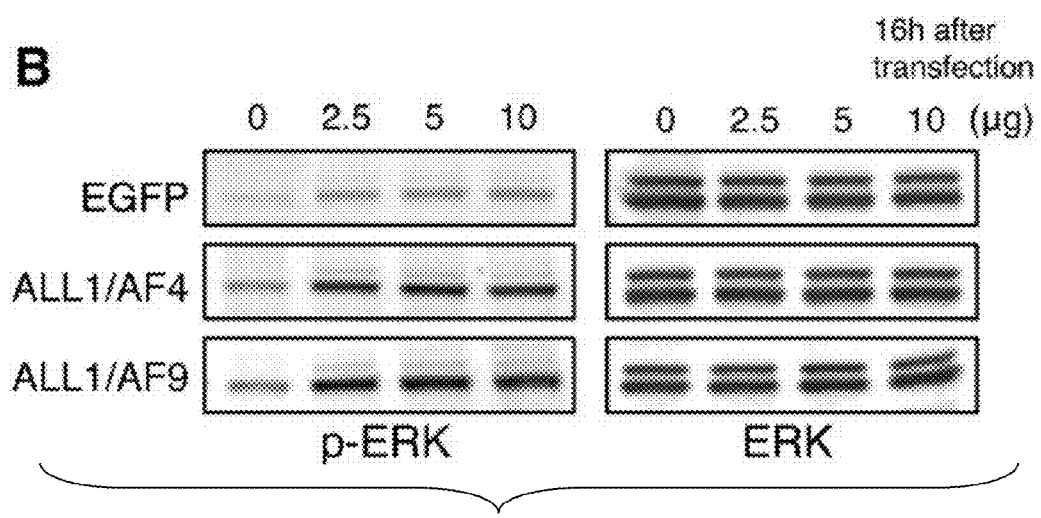

FIGS. 4A-4B: EphA7 mediates Erk phosphorylation:

FIG. 4A: K562 and KG1 cells transfected with the EphA7 construct were analyzed by Western blotting for determining the phosphorylation status of c-Raf, Mek1/2 and Erk, as well as for detection of the construct derived EphA7 protein. β-actin serves as a loading control.

FIG. 4B: The phosphorylation status of Erk was determined in K562 cells transfected with ALL1 fusion construct.

Figure 4C:
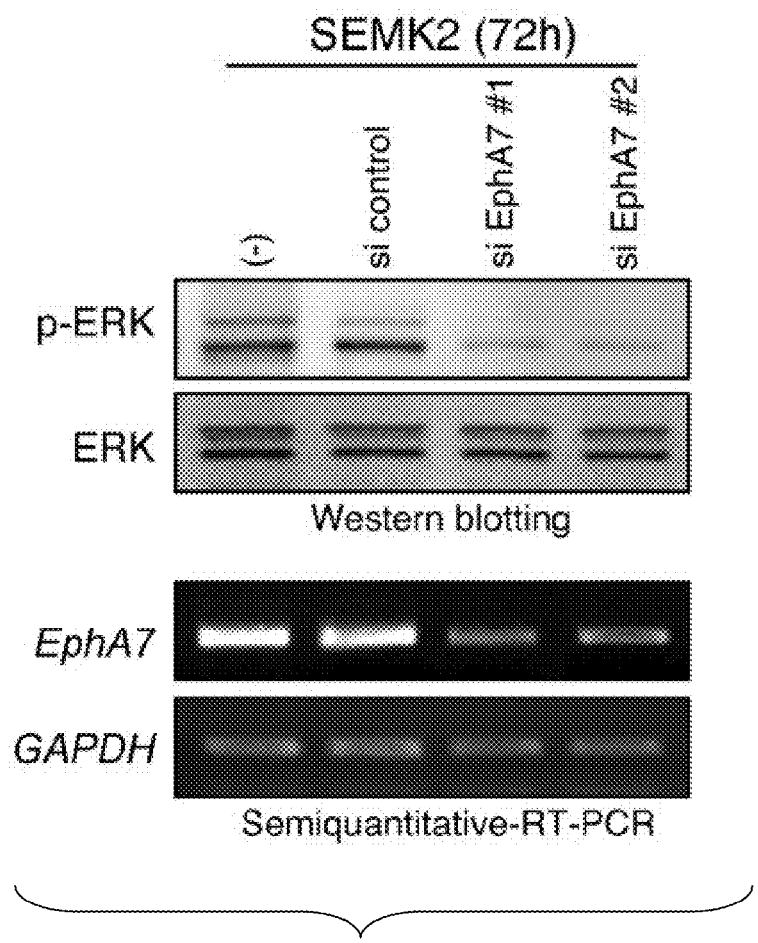
Figure 4D:
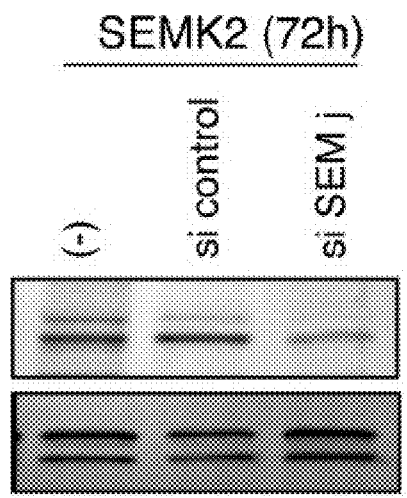

FIGS. 4C-4D: SEMK2 cells, suppressed for the expression of EphA7 by treatment with EphA7 specific siRNAs (siEphA7#1 and #2 in FIG. 4C or by treatment with ALL1/AF4 specific siRNA (FIG. 4D) were analyzed for Erk phosphorylation status. The efficiency of siEphA7#1 and #2 for EphA7 suppression was determined by semi-quantitative RT-PCR (FIG. 4C, bottom).

Figure 5A:
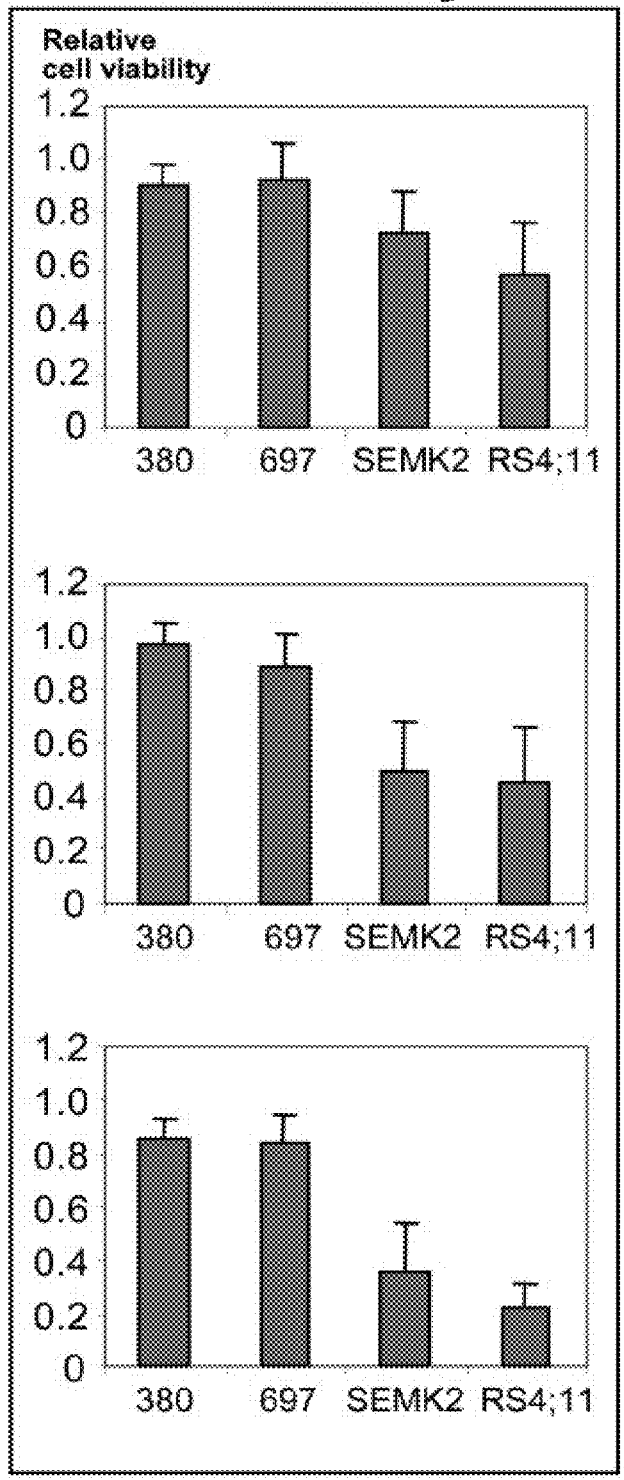
Figure 5B:
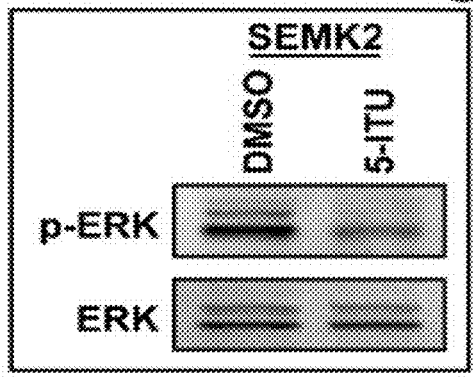
Figure 5B:
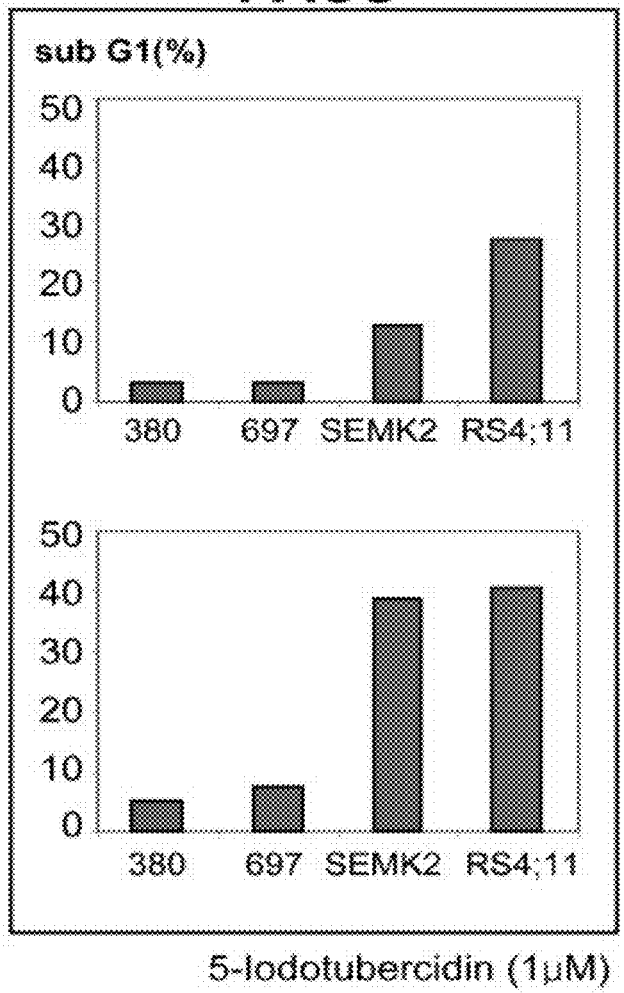
Figure 5C:
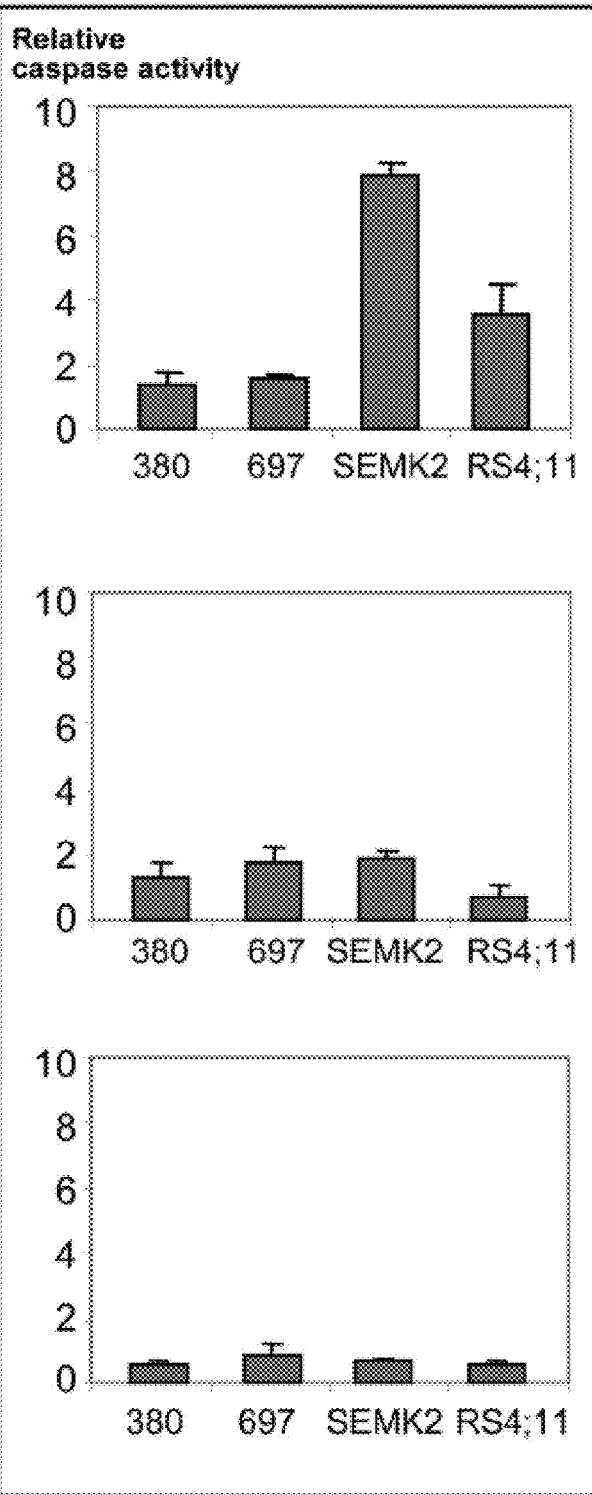

FIGS. 5A-5C: 5-iodotubercidin specifically inhibits Erk phosphorylation and the growth of the cells producing All1/Af4 fusion protein. SEMK2 cells with the t(4;11) treated for 24 hr with either solvent (DMSO) or 5 µM 5-iodotubercidin (5-ITU) were subjected to Western blot analysis for the detection of phosphorylated Erk. The SEMK2 and RS4;11 pro-B leukemic cell lines with the t(4;11), and the pro-B line 380 and pre-B line 697 lacking ALL1 abnormality were treated with 1 µM 5-ITU for 24, 48 and 72 hr (top, middle and bottom, respectively). At each time point, the cells were subjected to MTT assay (left), Caspase 3 activity assay (middle) and FACS analysis (right). The results of MTT and Caspase 3 activity assays are calculated as a ratio against the value for DMSO-treated cells. Vertical bar in each column indicates standard deviation determined by triplicate assays.

DETAILED DESCRIPTION OF THE PREFERRED EMBODIMENT

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The inventor herein has now discovered a correlation between the expression of certain receptors and ligands in ALL1-associated leukemias. In particular, there is now described herein the discovery of a correlation between the expression of EphA receptors and ligands in ALL1-associated leukemias.

Eph receptor tyrosine kinases and their cell surfacebound ligands, the ephrins, function as a unique signaling system triggered by cell to cell interaction, and have been shown to mediate neurodevelopmental processes. In addition, recent studies showed de-regulation of some of Eph/ephrin genes in human malignancies, suggesting the involvement of this signaling pathway in tumorigenesis.

The erythropoietin-producing hepatoma amplified sequence (Eph) receptors are a large family of receptor tyrosine kinases comprising 8 EphA and 6 EphB receptors in humans. The distinction between EphA and B receptors is based on the similarity within each group of the extracellular domain sequences and on the affinity for binding ephrin-A and ephrin-B ligands. Thus, EphA receptors bind to the ligands, termed ephrin-A1, -A2, -A3, -A4 and -A5 anchored on cell membrane via glycosylphosphatidylinositol, whereas EphB receptors bind to the ligands termed ephrin-B1, -B2 and -B3, which are transmembrane molecules. Since both the Eph receptors and the ephrins localize to the cell surface, the signaling is restricted to the sites of direct cell to cell contact, and is capable of inducing reciprocal bidirectional events between interacting cells. This unique feature has been shown to play a critical role in establishing topologically organized neuronal connections in many regions of the developing nervous system. Recent studies further unveiled the involvement of Eph-ephrin interaction in a variety of developmental processes including arterial-venous differentiation, cell migration which results in compartmentalizing cell subpopulations in the developing tissue and cell movement into the appropriate embryonic environment which may determine a particular cell fate and result in cell differentiation and patterning (reviewed in ref. 1). Beside such physiological roles, recent studies revealed deregulation of some of the Eph/ephrin genes in human malignancies. These include upregulation of ephrin-A1 or -B2 in melanoma (2, 3), upregulation of EphB2 in stomach cancer (4) and in breast cancer (5), upregulation of EphA2 in prostate (6), breast (7) and esophageal cancers (8), some of which were shown to be associated with tumor invasion or tumor metastasis and therefore associated with poor prognosis.

Conversely, mutational inactivation of EphB2 was detected in prostate (9) and colon cancers (10), suggesting tumor suppressor function of this Eph receptor in the relevant tumors. In contrast to solid tumors, less is known about the role of Eph/ephrin pathway in the development of hematological malignancies.

While EphA7 is expressed in fetal bone marrow pro-B and pre-B cells, it is silenced in the entire series of adult B-lineage cells (13). Until now, there has been no correlation between the expression of EphA receptors and ligands in ALL1-associated leukemias.

The inventor herein now demonstrates that EphA7 upregulation is accompanied by Erk phosphorylation. Also, apoptotic cell death, specific for leukemic cells carrying the t(4;11) chromosome translocation, following treatment of the cells with an Erk phosphorylation blocker.

In a broad aspect, the inventor herein searched for expression of EphA receptors in cells producing All1/Af4 and All1/Af9 fusion proteins, and found that both proteins induced EphA7 transcription.

Chromatin immunoprecipitation analysis demonstrated the occupancy of the fusion proteins on the EphA7 promoter, indicating EphA7 as a direct target of All1 fusion proteins. Consistent with those results, All1/Af4-dependent EphA7 expression was demonstrated in a pro-B cell line with the t(4;11).

Furthermore, direct EphA7 knockdown or All1/Af4 knockdown-mediated EphA7 suppression in the t(4;11) leukemic cells resulted in attenuation of Erk1/2 phosphorylation.

In addition, treatment of leukemic cells carrying the t(4;11) with an inhibitor of Erk phosphorylation induced apoptotic cell death.

These results indicate that the All1 fusion proteins directly upregulate EphA7 expression, which apparently results in Erk phosphorylation. The latter modification is likely to contribute to the maintenance of the malignant phenotype.

EXAMPLES

Screening of K562 cells producing recombinant All1/Af4 or All1/Af9 fusion protein revealed transcriptional upregulation of the EphA7. Consistent with this finding, siRNA mediated suppression of All1/Af4 in SEMK2 cells carrying the t(4;11) chromosome translocation resulted in downregulation of EphA7. Chromatin immunoprecipitation analysis demonstrated the occupancy of tagged All1 fusion proteins on the EphA7 promoter, pointing EphA7 as a direct target of the former.

Results

All1 Fusion Proteins Induce EphA7 Receptor Expression.

By applying a transfection strategy to ectopically express All1/Af4 and All1/Af9 in K562 cells (FIG. 1A, bottom, left), the expression level of the genes encoding 8 EphA receptors and 5 ephrin-A ligands in the transfectants was determined. Semi-quantitative RT-PCR analysis showed that both All1 fusion proteins induced transcription of all EphA receptor genes, while they did not exert a noticeable effect on induction of ephrin-A genes (FIG. 1A).

To further extend this finding to leukemic cells with ALL1 rearrangement, the SEMK2 and RS4;11 pro-B cell lines harboring the t(4;11) translocation, and the 380 pro-B and 697 pre-B cell lines lacking ALL1 abnormalities were subjected to similar analysis (FIG. 1B).

This analysis showed consistent and differential expression of EphA7 in the t(4;11) leukemic cell lines. Subsequent quantification of EphA7 transcript by application of real time RT-PCR methodology enabled estimation of the amounts of the transcript in K562 cells transfected with ALL1/AF4 or ALL1/AF9, in SEMK2 and in RS4;11 cells to be 0.04+0.01, 0.014+0.006, 1.97+0.6, and 0.68+0.09 (mean+SD femtogram), respectively.

In parallel, the amount of EphA7 RNA in vector-transfected K562, intact 380 and 697 cells were determined to be less than 0.001 fg (FIG. 1C).

These results collectively pointed EphA7 as a consistently responsive target of All1 fusion proteins, and prompted further analysis of its upregulation. To ascertain that the endogenous All1 fusion protein produced in leukemic cells carrying an ALL1 abnormality regulates EphA7 transcription, we suppressed All1/Af4 produced in SEMK2 cells by applying small interfering RNA (siRNA) methodology. SEMj siRNA generated by the inventor herein (14) and others (15) is designed to target SEMK2 cell-specific ALL1/AF4 fusion junction; in parallel, MVj siRNA targets the fusion junction produced in other cells (MV4;11), and thus served as a negative control. We first determined the efficiency of SEMj siRNA in suppressing the All1/Af4 protein and found approx. 80% reduction of the latter, with no effect on the expression level of normal All1 or Af4 (FIG. 2A).

SEMK2 cells treated with SEMj siRNA were then subjected to semi-quantitative RT-PCR analysis to determine the expression level of EphA7 as well as of HoxA9; the latter is a known target of All1 fusion proteins (16) and thus served as a positive control to ascertain the effect of elimination of the All1 fusion protein. This analysis demonstrated that the suppression of the All1/Af4 in SEMK2 cells attenuated expression of EphA7 and HoxA9, supporting the notion of All1 fusion protein-mediated transcriptional regulation of EphA7 (FIG. 2B).

All1-Fusion Proteins Bind to EphA7 Genomic Locus.

By applying chromatin immunoprecipitation (ChIP) methodology, we determined the occupancy of HA-tagged All1/Af4 and All1/Af9 exogenously expressed in K562 cells. The EphA7 genomic regions analyzed by ChIP mapped around 0.7 kb upstream and 0.6 kb downstream from the transcription initiation site, and within 3' non-coding sequence; they were termed region #1, #2 and #3, respectively (FIG. 3A).

This analysis showed the binding of the All1/Af4 and All1/Af9 chimeric proteins to region #1 and #2, but not to region #3 (FIG. 3B).

Quantitative real time PCR analysis supported the previous results (FIG. 3C), indicating that EphA7 is a direct target of the All1 fusion proteins.

EphA7 is an Essential Mediator in Induction of Erk Phosphorylation.

Little is known about the signal transduction pathway(s) in which EphA7 is involved. At first, we examined in K562 cells transfected with full length EphA7 construct the phosphorylation status of several proteins commonly associated with RTK-signal transduction pathways. Consistent with previous results (see FIG. 1A, right), the EphA7 protein was not observed in intact K562 cells, but was detected in a dose-dependent manner in cells transfected with the EphA7 construct (FIG. 4A, left).

We found no apparent induction of c-Raf or Mek1/2 phosphorylation, two proteins that are phosphorylated in response to activation of the Ras transduction pathway (FIG. 4A, left).

In contrast, we found that overexpressing EphA7 correlated with Erk phosphorylation. This was determined by sequential probing of a Western blot with anti-Erk Ab and subsequently with antibody against phosphorylated-Erk which specifically detect p-Erk (FIG. 4A, left).

It was previously shown that Mek1/2 are highly phosphorylated in intact K562 cells (17). Such basic high Mek1/2 phosphorylation may have obscured an additional change in phosphorylation induced by overexpressing EphA7. Therefore, we ectopically expressed EphA7 in the KG1 AML cell line. Here we found induction of Mek1/2 phosphorylation, following expression of recombinant EphA7 (FIG. 4A, right).

We also noticed that the Mek1/2 phosphorylation in KG1 cells was accompanied by Erk2 as well as Erk1 phosphorylation (FIG. 4A, right).

Since the prominent function of Mek is to phosphorylate Erk (18), our results indicate that EphA7 is positioned upstream to this cascade.

We next determined whether All1 fusion proteins induce Erk phosphorylation as EphA7 does. Indeed, induction of Erk phosphorylation was observed in K562 cells transfected with the ALL1/AF4 and ALL1/AF9 constructs (FIG. 4B).

To validate that in these transfectants EphA7 is an essential mediator for Erk phosphorylation, SEMK2 cells were treated with siRNAs targeting EphA7 mRNA at two distinct regions within the transcript (siEphA7#1 and #2 in FIG. 4C).

Both siRNAs were shown to downregulate the mRNA at an efficiency of ~70% (FIG. 4C, bottom). Suppression of EphA7 resulted in strong reduction of Erk1 and Erk2 phosphorylation, with no effect on the amount of total Erk (FIG. 4C, top).

This implied that EphA7 is an essential mediator for Erk1/2 phosphorylation in cells expressing All1 fusions. Furthermore, we found that All1/Af4 knockdown in SEMK2 cells similarly caused reduced phosphorylation of Erk1/2 (FIG. 4D).

An Inhibitor For ERK2 Phosphorylation, 5-iodotubercidin, Induces Cell Death of Leukemic Cell Lines With the t(4;11) Abnormality.

We examined the effect of 5-iodotubercidin (5-ITU), an inhibitor for Erk phosphorylation (19), on cell proliferation. To ascertain the biochemical effect of 5-ITU, SEMK2 cells with the t(4;11) and producing phosphorylated Erk1/2 (see "-" and "si control" lanes in FIGS. 4C and D) were treated with this compound and Erk phosphorylation status was determined by Western blot analysis (FIG. 5, top, right).

The result indicated inhibition of Erk phosphorylation by 5-ITU. Application of the MTT assay indicated reduction in numbers of SEMK2 and RS4;11 cells with the t(4;11), with no diminution in the number of the 380 and 697 control cells (FIG. 5, left). We also found that All1/Af4 knockdown in SEMK2 cells, which caused Erk1/2 inactivation (see FIG. 4D), resulted in approx. 25% reduction in the cell number as compared to the number of cells treated with control siRNA (H. Nakanishi, unpublished result). To determine the cause for the reduction in cell numbers, the 5-ITU-treated cells were subjected to assays determining apoptotic cell death (caspase 3 activity assay and FACS analysis). Increased caspase 3 activity was demonstrated at 24 hr in 5-ITU sensitive leukemic cells (SEMK2 and RS4;11 in FIG. 5B). In parallel, a high proportion of these cells distributed at the subG1 phase (FIG. 5C). These results demonstrated dependency of the leukemic cells producing All1/Af4 fusion protein on Erk phosphorylation, with the latter preventing apoptotic cell death.

Discussion

In the present study, we showed that ectopic expression in K562 cells of the leukemogenic All1 fusion proteins All1/Af4 and All1/Af9, induced transcription of several EphA RTKs after a short latency (16 hr after transfection). Significantly, applying such approach to induce HoxA9 did not work. Thus, we found that ectopic expression of All1/Af4 or All1/Af9 did not induce HoxA9 expression, and that further treatment of the transfectants with the HDAC inhibitor trichostatin A was required (T. Nakamura, unpublished data). Therefore, it appears that additional layer(s) of transcriptional regulation is involved in induction of HoxA9 by All1 fusion proteins. We note that deregulation of EphA7 was not mentioned in previous studies of gene expression profiling of ALL1-associated acute leukemias (20, 21).

A recent review concerning Eph receptors and ephrin signaling (ref. 1) showed the involvement of a wide variety of pathways, including examples for activation or inhibition of several different signaling pathways by a single Eph receptor. Presently, however, signaling pathways involved in EphA7 RTK have not been determined. In this study, we examined the phosphorylation status of the major components of the MAPK/Erk pathway including c-Raf, Mek1/2 and Erk in K562 cells expressing either of two exogenous All1 fusion proteins or EphA7. The three proteins induced Erk phosphorylation. We also noticed Erk phosphorylation in a control transfection with EGFP construct, although the extent of the phosphorylation induced by the latter is less than ⅕ of that induced by the All1 fusion proteins (see FIG. 4B).

Furthermore, siRNA mediated suppression directed against either All1/Af4 or EphA7 in SEMK2 cells resulted in remarkable reduction of Erk phosphorylation (see FIGS. 4C and 4D). These results indicate that EphA7 indeed mediates Erk phosphorylation in K562 transfectants and in SEMK2 cells. No induction of c-Raf and Mek1/2 phosphorylation by EphA7 was observed in K562 cells (see FIG. 4A). However, a further study with KG1 cells showed EphA7-mediated Mek1/2 phosphorylation, accompanied with induction of Erk1/2 phosphorylation. It is therefore likely that EphA7 activates Mek1/2, leading to Erk phosphorylation. However, we cannot exclude the possibility that Erk phosphorylation mediated by EphA7 in K562 is executed by a pathway different from the classical MAPK/Erk. Regarding this issue, two studies suggest the presence of MEK-independent pathways (22, 23).

Because of the absence of antibodies for specific detection of phosphorylated EphA7, we could not determine whether EphA7 induced by ectopic All1 fusion protein or recombinant EphA7 in K562 and endogenous EphA7 in SEMK2 cells are present in an active phosphorylated form. A study of in vitro ephrin-A ligand-receptor binding assay previously showed that EphA7 displays high affinity to ephrin-A3 and -A5 ligands (24).

In the present study, we found a steady level of ephrin-A3 expression in K562 cells transfected either with control empty vector or with All1 fusion construct (see FIG. 1).

It is therefore likely that EphA7 expressed in K562 cells interacts with the ephrin-A3 ligand produced in the same cells and affecting activation of the Eph/ephrin pathway. Furthermore, Erk phosphorylation caused by overexpression of EphA7 in K562 cells, and reduced Erk1/2 phosphorylation caused by suppression of EphA7 in SEMK2 cells, suggest that the EphA7 protein in either circumstance is active.

Expression of Eph receptors including EphA7 is tightly regulated. A previous study to determine EphA7/Hek11 expression in human hematopoietic cells showed regulated expression of the gene in fetal bone marrow pro- and pre-B cells, but not in adult bone marrow cells of the same differential stages (13). Consistent with these results, we also found that EphA7 expression level in 380 pro-B and 697 pre-B cell lines as well as in intact K562 cells was below detection limit (0.001 fg>) as assayed by real time RT-PCR methodology. The detection of EphA7 in the pro-B cell lines SEMK2 and RS4;11 would further argue that All1/Af4 upregulates EphA7 expression in pro-B cells.

We found that 5-ITU suppressed growth of the leukemic cells producing All1/Af4 fusion protein by inducing apoptosis. 5-ITU was originally discovered as a potent inhibitor of adenosine kinase (Ki=30 nM), Ser/Thr-specific kinases such as casein kinases 1 and 2, and the insulin receptor kinase fragment. The Ki for inhibition of ERK2 phosphorylation was estimated to be 525 nM (19). It is therefore possible that the treatment of the cells with 1 µM 5-ITU not only caused inactivation of Erk but also affected the aforementioned kinases. Regardless of this, the differential apoptotic effect on two cell lines with t(4;11) was clear.

Materials and Methods

Methods including Recombinant protein expression in K562 and in KG1 cells, RNA interference, Western blot analysis, and MTT assay, Caspase 3 Activity assay and FACS analysis are available in online Supporting Information.

Cell Lines

The human erythroleukemia cell line K562, the AML cell line KG1 and the pro-B ALL cell line RS4;11 with the t(4;11) abnormality were obtained from ATCC. The SEMK2 line was provided by Dr. Johann Greil. Other ALL cell lines selected for this study (380, 697) are maintained in our laboratory. All cell lines were grown in RPMI-1640 medium supplemented with 10% fetal calf serum.

Semi-Quantitative and Real Time RT-PCR Analysis

Total RNA was isolated from transfectant 16 hr after transfection by using RNeasy spin-column kits according to the manufacturer's instructions (Qiagen, Valencia, Calif.). 5 µg of total RNA was subjected to cDNA synthesis by using SuperScript™ III First-Strand Synthesis System (Invitrogen, Carlsbad, Calif.). At the end of the reaction, 40 µL of TE (10 mM Tris, 1 mM EDTA, pH7.6) was added and 1 µL of the reaction (1/60 volume) was used as a template for PCR. The following numbers of cycles, which allowed semi-quantitative comparison, were applied to PCR: 35 cycles for EphA1, 2, 4, 7, 8 and ephrin-A1, 2, 3, 4, 5; 40 cycles for EphA3, 5, 6; 25 cycles for GAPDH; 32 cycles for HoxA9.

EphA7 transcript was quantified by using QuantiTect SYBR Green RT-PCR kit (QIAGEN) for the amplification of cDNA (1 µL cDNA out of 60 µL reaction, which corresponds to 0.083 µg RNA) and iCycler real-time PCR detection system (BioRad) for the detection of PCR product. Cycle threshold (Ct) values determined by using known amounts of EphA7 cDNA (10-fold serial dilutions starting at 100 pg) were used to construct the standard curve. Ct value of the tested cDNA was converted to weight according to the standard curve.

Chromatin Immunoprecipitation (ChIP) Assay

ChIP assay was done by using the ChIP assay kit of Upstate Biotechnology (Lake Placid, N.Y.). 16 hr after transfection with the ALL1 fusion constructs, 5×106 cells (K562 transfectants) were cross-linked, washed with PBS, resuspended in 1 ml of SDS lysis buffer and sonicated to generate approx. 200-1000 bp DNA fragments. 1/10 volume of this preparation, i.e. 0.1 mL aliquot containing 25 µg DNA, was used per ChIP. Antibodies used were anti-HA mAb clone F-7, and normal mouse IgG purchased from Santa Cruz Biotech Immunoprecipitated chromatin was reverse cross-linked, deproteinized and resuspended in 50 µL of TE, pH 8.0 and 1 µL aliquot of this preparation was used as a template for PCR. Input indicates PCR reaction using 0.05% of total input chromatin, which corresponds to 0.0125 µg DNA. EphA7 primer sequences used in ChIP assay are:

```
region #1
(forward)
                                    [SEQ ID NO: 4]
5'-ATGCAGCGAAATGGAAAACT-3',
and (reverse)
                                    [SEQ ID NO: 1]
5'-AAAAGGGAGTGGGAAAGGAA-3' region #2
(forward)
                                    [SEQ ID NO: 5]
5'-TAGTACCTCAGGCGGGTCAC-3',
and (reverse)
                                    [SEQ ID NO: 2]
5'-TTCCGAGCTCATCGAAGTCT-3' region #3
(forward)
                                    [SEQ ID NO: 6]
5'-TTGTCGTTGGACGTTCACAT-3',
and (reverse)
                                    [SEQ ID NO: 3]
5'-CAATAGCGCCTCATCTGACA-3'.
```

ChIP-enriched DNA was subjected as well to real-time PCR analysis essentially as described in "Semi-quantitative and Real Time RT-PCR analysis". Results were calculated as % of input according to the following formula: 100/2Ct of ChIP-enriched DNA-Ct of Input DNA (%).

Examples of Uses

In one aspect, the present invention provides methods for predicting survival of a subject with cancer. The prediction method is based upon the differential expression of a plurality of biomarkers in cancer cells. It was discovered that some biomarkers tend to be over-expressed in short-term cancer survivors, whereas other biomarkers tend to be over-expressed in long-term cancer survivors. The unique pattern of expression of these biomarkers in a sample of cells from a subject with cancer may be used to predict relative survival time, and ultimately the prognosis, for that subject.

One Method for Predicting Survival of a Subject With Cancer

One aspect of the invention provides a method for predicting cancer survival. The method comprises determining the differential expression of a plurality of biomarkers in a sample of cells from a subject with cancer. The biomarker expression signature of the cancer may be used to derive a risk score that is predictive of survival from that cancer. The score may indicate low risk, such that the subject may survive a long time (i.e., longer than 5 years), or the score may indicate high risk, such that the subject may not survive a long time (i.e., less than two years).

Survival-Related Biomarkers

Some of the biomarkers are over-expressed in long-term survivors and some of the biomarkers are over-expressed in short-term survivors. A biomarker may play a role in cancer metastasis by affecting cell adhesion, cell motility, or inflammation and immune responses. A biomarker may also be involved in apoptosis. A biomarker may play a role in transport mechanism. A biomarker may also be associated with survival in other types of cancer Measuring Expression Of A Plurality Of Biomarkers One includes entails measuring the differential expression of a plurality of survival-related biomarkers in a sample of cells from a subject with cancer. The differential pattern of expression in each cancer—or gene expression signature—may then be used to generate a risk score that is predictive of cancer survival. The level of expression of a biomarker may be increased or decreased in a subject relative to other subjects with cancer. The expression of a biomarker may be higher in long-term survivors than in short-term survivors. Alternatively, the expression of a biomarker may be higher in short-term survivors than in long-term survivors.

The differential expression of a plurality of biomarkers may be measured by a variety of techniques that are well known in the art. Quantifying the levels of the messenger RNA (mRNA) of a biomarker may be used to measure the expression of the biomarker. Alternatively, quantifying the levels of the protein product of a biomarker may be to measure the expression of the biomarker. Additional information regarding the methods discussed below may be found in Ausubel et al., (2003) Current Protocols in Molecular Biology, John Wiley & Sons, New York, N.Y., or Sambrook et al. (1989). Molecular Cloning: A Laboratory Manual, Cold Spring Harbor Press, Cold Spring Harbor, N.Y. One skilled in the art will know which parameters may be manipulated to optimize detection of the mRNA or protein of interest.

A nucleic acid microarray may be used to quantify the differential expression of a plurality of biomarkers. Microarray analysis may be performed using commercially available equipment, following manufacturer's protocols, such as by using the Affymetrix GeneChip® technology (Santa Clara, Calif.) or the Microarray System from Incyte (Fremont, Calif.). Typically, single-stranded nucleic acids (e.g., cDNAs or oligonucleotides) are plated, or arrayed, on a microchip substrate. The arrayed sequences are then hybridized with specific nucleic acid probes from the cells of interest. Fluorescently labeled cDNA probes may be generated through incorporation of fluorescently labeled deoxynucleotides by reverse transcription of RNA extracted from the cells of interest. Alternatively, the RNA may be amplified by in vitro transcription and labeled with a marker, such as biotin. The labeled probes are then hybridized to the immobilized nucleic acids on the microchip under highly stringent conditions. After stringent washing to remove the non-specifically bound probes, the chip is scanned by confocal laser microscopy or by another detection method, such as a CCD camera. The raw fluorescence intensity data in the hybridization files are generally preprocessed with the robust multichip average (RMA) algorithm to generate expression values.

Quantitative real-time PCR (QRT-PCR) may also be used to measure the differential expression of a plurality of biomarkers. In QRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified. A non-limiting example of a fluorescent reporter probe is a TaqMan® probe (Applied Biosystems, Foster City, Calif.). The fluorescent reporter probe fluoresces when the quencher is removed during the PCR extension cycle. Muliplex QRT-PCR may be performed by using multiple gene-specific reporter probes, each of which contains a different fluorophore. Fluorescence values are recorded during each cycle and represent the amount of product amplified to that point in the amplification reaction. To minimize errors and reduce any sample-to-sample variation, QRT-PCR is typically performed using a reference standard. The ideal reference standard is expressed at a constant level among different tissues, and is unaffected by the experimental treatment. Suitable reference standards include, but are not limited to, mRNAs for the housekeeping genes glyceraldehyde-3-phosphate-dehydrogenase (GAPDH) and beta-actin. The level of mRNA in the original sample or the fold change in expression of each biomarker may be determined using calculations well known in the art.

Immunohistochemical staining may also be used to measure the differential expression of a plurality of biomarkers. This method enables the localization of a protein in the cells of a tissue section by interaction of the protein with a specific antibody. For this, the tissue may be fixed in formaldehyde or another suitable fixative, embedded in wax or plastic, and cut into thin sections (from about 0.1 mm to several mm thick) using a microtome. Alternatively, the tissue may be frozen and cut into thin sections using a cryostat. The sections of tissue may be arrayed onto and affixed to a solid surface (i.e., a tissue microarray). The sections of tissue are incubated with a primary antibody against the antigen of interest, followed by washes to remove the unbound antibodies. The primary antibody may be coupled to a detection system, or the primary antibody may be detected with a secondary antibody that is coupled to a detection system. The detection system may be a fluorophore or it may be an enzyme, such as horseradish peroxidase or alkaline phosphatase, which can convert a substrate into a colorimetric, fluorescent, or chemiluminescent product. The stained tissue sections are generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for the biomarker.

An enzyme-linked immunosorbent assay, or ELISA, may be used to measure the differential expression of a plurality of biomarkers. There are many variations of an ELISA assay. All are based on the immobilization of an antigen or antibody on a solid surface, generally a microtiter plate. The original ELISA method comprises preparing a sample containing the biomarker proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. For this, the primary antibodies are conjugated to a detection system, such as an enzyme that produces a detectable product. The antibody-antibody complexes may be detected indirectly. For this, the primary antibody is detected by a secondary antibody that is conjugated to a detection system, as described above. The microtiter plate is then scanned and the raw intensity data may be converted into expression values using means known in the art.

An antibody microarray may also be used to measure the differential expression of a plurality of biomarkers. For this, a plurality of antibodies is arrayed and covalently attached to the surface of the microarray or biochip. A protein extract containing the biomarker proteins of interest is generally labeled with a fluorescent dye. The labeled biomarker proteins are incubated with the antibody microarray. After washes to remove the unbound proteins, the microarray is scanned. The raw fluorescent intensity data may be converted into expression values using means known in the art.

Luminex multiplexing microspheres may also be used to measure the differential expression of a plurality of biomarkers. These microscopic polystyrene beads are internally color-coded with fluorescent dyes, such that each bead has a unique spectral signature (of which there are up to 100). Beads with the same signature are tagged with a specific oligonucleotide or specific antibody that will bind the target of interest (i.e., biomarker mRNA or protein, respectively). The target, in turn, is also tagged with a fluorescent reporter. Hence, there are two sources of color, one from the bead and the other from the reporter molecule on the target. The beads are then incubated with the sample containing the targets, of which up to 100 may be detected in one well. The small size/surface area of the beads and the three dimensional exposure of the beads to the targets allows for nearly solution-phase kinetics during the binding reaction. The captured targets are detected by high-tech fluidics based upon flow cytometry in which lasers excite the internal dyes that identify each bead and also any reporter dye captured during the assay. The data from the acquisition files may be converted into expression values using means known in the art.

In situ hybridization may also be used to measure the differential expression of a plurality of biomarkers. This method permits the localization of mRNAs of interest in the cells of a tissue section. For this method, the tissue may be frozen, or fixed and embedded, and then cut into thin sections, which are arrayed and affixed on a solid surface. The tissue sections are incubated with a labeled antisense probe that will hybridize with an mRNA of interest. The hybridization and washing steps are generally performed under highly stringent conditions. The probe may be labeled with a fluorophore or a small tag (such as biotin or digoxigenin) that may be detected by another protein or antibody, such that the labeled hybrid may be detected and visualized under a microscope. Multiple mRNAs may be detected simultaneously, provided each antisense probe has a distinguishable label. The hybridized tissue array is generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for each biomarker.

The number of biomarkers whose expression is measured in a sample of cells from a subject with cancer may vary. Since the predicted score of survival is based upon the differential expression of the biomarkers, a higher degree of accuracy should be attained when the expression of more biomarkers is measured.

Obtaining a Sample of Cells From a Subject With Cancer

The expression of a plurality of biomarkers will be measured in a sample of cells from a subject with cancer. The type and classification of the cancer can and will vary. The cancer may be an early stage cancer, i.e., stage I or stage II, or it may be a late stage cancer, i.e., stage III or stage IV.

Generally, the sample of cells or tissue sample will be obtained from the subject with cancer by biopsy or surgical resection. The type of biopsy can and will vary, depending upon the location and nature of the cancer. A sample of cells, tissue, or fluid may be removed by needle aspiration biopsy. For this, a fine needle attached to a syringe is inserted through the skin and into the organ or tissue of interest. The needle is typically guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue may also be removed by incisional or core biopsy. For this, a cone, a cylinder, or a tiny bit of tissue is removed from the region of interest. CT imaging, ultrasound, or an endoscope is generally used to guide this type of biopsy. Lastly, the entire cancerous lesion may be removed by excisional biopsy or surgical resection.

Once a sample of cells or sample of tissue is removed from the subject with cancer, it may be processed for the isolation of RNA or protein using techniques well known in the art and disclosed in standard molecular biology reference books, such as Ausubel et al., (2003) Current Protocols in Molecular Biology, John Wiley & Sons, New York, N.Y. A sample of tissue may also be stored or flash frozen and stored at −80° C. for later use. The biopsied tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. RNA or protein may also be extracted from a fixed or wax-embedded tissue sample.

The subject with cancer will generally be a mammalian subject. Mammals may include primates, livestock animals, and companion animals. Non-limiting examples include: Primates may include humans, apes, monkeys, and gibbons; Livestock animals may include horses, cows, goats, sheep, deer and pigs; Companion animals may include dogs, cats, rabbits, and rodents (including mice, rats, and guinea pigs). In an exemplary embodiment, the subject is a human.

Generating A Risk Score

The biomarkers of this invention are related to cancer survival. The differential patterns of expression of a plurality of these biomarkers may be used to predict the survival outcome of a subject with cancer. Certain biomarkers tend to be over-expressed in long-term survivors, whereas other biomarkers tend to be over-expressed in short-term survivors. The unique pattern of expression of a plurality of biomarkers in a subject (i.e., the expression signature) may be used to generate a risk score of survival. Subjects with a high risk score may have a short survival time (<2 years) after surgical resection. Subjects with a low risk score may have a longer survival time (>5 years) after resection.

Regardless of the technique used to measure the differential expression of a plurality of biomarkers, the expression of each biomarker typically will be converted into an expression value. These expression values then will be used to calculate a risk score of survival for a subject with cancer using statistical methods well known in the art. The risk scores may be calculated using a principal components analysis. The risk scores may also be calculated using a univariate Cox regression analysis. In one preferred embodiment, the risk scores may be calculated using a partial Cox regression analysis.

The scores generated by a partial Cox regression analysis fall into two groups: 1) those having a positive value; and 2) those having a negative value. A risk score having a positive value is associated with a short survival time, and a risk score having a negative value is associated with a long survival time.

In one embodiment of this method, a tissue sample may be removed by surgical resection from a subject with an early stage cancer. The sample of tissue may be stored in RNA later or flash frozen, such that RNA may be isolated at a later date. The RNA may be used as a template for QRT-PCR in which the expression of a plurality of biomarkers is analyzed, and the expression data are used to derive a risk score using the partial Cox regression classification method. The risk score may be used to predict whether the subject will be a short-term or a long-term cancer survivor.

In an especially preferred embodiment of this method, a sample of tissue may be collected from a subject with an early stage cancer. RNA may be isolated from the tissue and used to generate labeled probes for a nucleic acid microarray analysis. The expression values generated from the microarray analysis may be used to derive a risk score using the partial Cox regression classification method. The risk score may be used to predict whether the subject will be a short-term or a long-term cancer survivor.

Method For Determining the Prognosis of a Subject With Cancer

Another aspect of the invention provides a method for determining the prognosis of a subject with a cancer. The method comprises measuring the differential expression of one or more biomarkers in a sample of cells from the subject. The differential expression of each biomarker is converted into an expression value, and the expression values are used to derive a score for that subject using a statistical method, as detailed above. A score having a positive value is indicative of a poor prognosis or a poor outcome, whereas a score having a negative value is indicative of a good prognosis or a good outcome.

In one embodiment of this method, an expression signature for a subject with an early stage cancer is generated by nucleic acid microarray analysis, and the expression values are used to calculate a score. The calculated score may be used to predict whether the subject will have a good prognosis or a poor prognosis of cancer outcome.

Method For Selecting a Treatment For a Subject With Cancer

A further aspect of the invention provides a method for selecting an effective treatment for a subject with cancer. Once a risk score has been calculated for a subject, that information may be used to decide upon an appropriate course of treatment for the subject. A subject having a positive risk score (i.e., short survival time or poor prognosis) may benefit from an aggressive therapeutic regime. An aggressive therapeutic regime may comprise the appropriate chemotherapy agent or agents. An aggressive therapeutic regime may also comprise radiation therapy. The treatment regime can and will vary, depending upon the type and stage of cancer. A subject having a negative risk score (i.e., long survival time or good prognosis) may not need additional treatment, since the subject is not likely to develop a recurrent cancer.

The cells are maintained under conditions in which the one or more agents inhibits expression or activity of the microRNAs, inhibits expression of one or more target genes of the microRNAs, or inhibits a combination thereof, thereby inhibiting proliferation of the cell.

Methods of identifying an agent that can be used to inhibit proliferation of a cancer cell are also provided. The method comprises contacting one or more microRNAs with an agent to be assessed; contacting one or more target genes with an agent to be assessed; or contacting a combination thereof. If expression of the microRNAs is inhibited in the presence of the agent; of if expression of the target genes is enhanced in the presence of the agent, or a combination thereof occurs in the presence of the agent, then the agent can be used to inhibit proliferation of a follicular thyroid carcinoma cell.

Method of Identifying Therapeutic Agents

Also provided herein are methods of identifying an agent that can be used to treat a patient in need thereof. The method comprises contacting one or more microRNAs with an agent to be assessed; contacting one or more target genes of one or more microRNAs; or contacting a combination thereof. If expression of the microRNAs is inhibited in the presence of the agent; of if expression of the target genes is enhanced in the presence of the agent, or a combination thereof occurs in the presence of the agent, then the agent can be used to inhibit proliferation of a follicular thyroid carcinoma cell.

Agents that can be assessed in the methods provided herein include miRNA inhibitors. Other examples of such agents include pharmaceutical agents, drugs, chemical compounds, ionic compounds, organic compounds, organic ligands, including cofactors, saccharides, recombinant and synthetic peptides, proteins, peptoids, nucleic acid sequences, including genes, nucleic acid products, and antibodies and antigen binding fragments thereof. Such agents can be individually screened or one or more compound(s) can be tested simultaneously in accordance with the methods herein. Large combinatorial libraries of compounds (e.g., organic compounds, recombinant or synthetic peptides, peptoids, nucleic acids) produced by combinatorial chemical synthesis or other methods can be tested. Where compounds selected from a combinatorial library carry unique tags, identification of individual compounds by chromatographic methods is possible. Chemical libraries, microbial broths and phage display libraries can also be tested (screened) in accordance with the methods herein.

Kit For Predicting Survival or Prognosis of a Subject With Cancer

A further aspect of the invention provides kits for predicting survival or prognosis of a subject with cancer. A kit comprises a plurality of agents for measuring the differential expression of one or more biomarkers, means for converting the expression data into expression values, and means for analyzing the expression values to generate scores that predict survival or prognosis. The agents in the kit for measuring biomarker expression may comprise an array of polynucleotides complementary to the mRNAs of the biomarkers. In another embodiment, the agents in the kit for measuring biomarker expression may comprise a plurality of PCR probes and/or primers for QRT-PCR.

The invention is also directed to kits for detecting a cancer an individual comprising one or more reagents for detecting 1) one or more microRNAs; 2) one or more target genes of one or more microRNAs; 3) one or more polypeptides expressed by the target genes or 4) a combination thereof. For example, the kit can comprise hybridization probes, restriction enzymes (e.g., for RFLP analysis), allele-specific oligonucleotides, and antibodies that bind to the polypeptide expressed by the target gene.

In a particular embodiment, the kit comprises at least contiguous nucleotide sequence that is substantially or completely complementary to a region of one or more of the microRNAs. In one embodiment, one or reagents in the kit are labeled, and thus, the kits can further comprise agents capable of detecting the label. The kit can further comprise instructions for detecting a cancer using the components of the kit.

Nucleic Acid Array

Another aspect of the invention provides for a nucleic acid array comprising polynucleotides that hybridize to the mRNAs of biomarkers of the invention. Generally speaking, the nucleic acid array is comprised of a substrate having at least one address. Nucleic acid arrays are commonly known in the art, and moreover, substrates that comprise nucleic acid arrays are also well known in the art. Non-limiting examples of substrate materials include glass and plastic. A substrate may be shaped like a slide or a chip (i.e. a quadrilateral shape), or alternatively, a substrate may be shaped like a well.

The array of the present invention is comprised of at least one address, wherein the address has disposed thereon a nucleic acid that can hybridize to the mRNA of a biomarker of the invention. In one embodiment, the array is comprised of multiple addresses, wherein each address has disposed thereon a nucleic acid that can hybridize to the mRNA of a biomarker for predicting survival of a subject with a lung cancer. The array may also comprise one or more addresses wherein the address has disposed thereon a control nucleic acid. The control may be an internal control (i.e. a control for the array itself) and/or an external control (i.e. a control for the sample applied to the array). An array typically is comprised from between about 1 to about 10,000 addresses. In one embodiment, the array is comprised from between about 10 to about 8,000 addresses. In another embodiment, the array is comprised of no more than 500 addresses. In an alternative embodiment, the array is comprised of no less than 500 addresses. Methods of using nucleic acid arrays are well known in the art.

Methods of Use

In one aspect, there is provided herein a method of diagnosing whether a subject has, or is at risk for developing acute lymphoblastic leukemia (ALL), comprising measuring the level of at least one gene product in a test sample from the subject and comparing the level of the gene product in the test sample to the level of a corresponding gene product in a control sample. As used herein, a "subject" can be any mammal that has, or is suspected of having, breast cancer. In a particular embodiment, the subject is a human who has, or is suspected of having, ALL.

The level of at least one gene product can be measured in cells of a biological sample obtained from the subject. For example, a tissue sample can be removed from a subject suspected of having ALL by conventional biopsy techniques. In another example, a blood sample can be removed from the subject, and white blood cells can be isolated for DNA extraction by standard techniques. The blood or tissue sample is preferably obtained from the subject prior to initiation of radiotherapy, chemotherapy or other therapeutic treatment. A corresponding control tissue or blood sample can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of gene product produced from a given gene in cells from the subject's sample can be compared to the corresponding gene product levels from cells of the control sample.

An alteration (i.e., an increase or decrease) in the level of a gene product in the sample obtained from the subject, relative to the level of a corresponding gene product in a control sample, is indicative of the presence of ALL in the subject. In one embodiment, the level of the at least one gene product in the test sample is greater than the level of the corresponding gene product in the control sample (i.e., expression of the gene product is "up-regulated"). As used herein, expression of a gene product is "up-regulated" when the amount of gene product in a cell or tissue sample from a subject is greater than the amount of the same gene product in a control cell or tissue sample. In another embodiment, the level of the at least one gene product in the test sample is less than the level of the corresponding gene product in the control sample (i.e., expression of the gene product is "down-regulated"). As used herein, expression of a gene is "down-regulated" when the amount of gene product produced from that gene in a cell or tissue sample from a subject is less than the amount produced from the same gene in a control cell or tissue sample. The relative gene expression in the control and normal samples can be determined with respect to one or more RNA expression standards. The standards can comprise, for example, a zero gene expression level, the gene expression level in a standard cell line, or the average level of gene expression previously obtained for a population of normal human controls.

The level of a gene product in a sample can be measured using any technique that is suitable for detecting RNA expression levels in a biological sample. Suitable techniques for determining RNA expression levels in cells from a biological sample (e.g., Northern blot analysis, RT-PCR, in situ hybridization) are well known to those of skill in the art. In a particular embodiment, the level of at least one gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, *Molecular Cloning: A Laboratory Manual*, J. Sambrook et al., eds., 2nd edition, Cold Spring Harbor Laboratory Press, 1989, Chapter 7, the entire disclosure of which is incorporated by reference.

Suitable probes for Northern blot hybridization of a given gene product can be produced from the nucleic acid sequences of the given gene product. Methods for preparation of labeled DNA and RNA probes, and the conditions for hybridization thereof to target nucleotide sequences, are described in *Molecular Cloning: A Laboratory Manual*, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^{3}H$, $^{32}P$, $^{33}P$, $^{14}C$, or $^{35}S$; a heavy metal; or a ligand capable of functioning as a specific binding pair member for a labeled ligand (e.g., biotin, avidin or an antibody), a fluorescent molecule, a chemiluminescent molecule, an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^{8}$ cpm/microgram. Autoradiographic detection of hybridization can then be performed by exposing hybridized filters to photographic film. Densitometric scanning of the photographic films exposed by the hybridized filters provides an accurate measurement of gene transcript levels. Using another approach, gene transcript levels can be quantified by computerized imaging systems, such the *Molecular Dynamics 400-B 2D Phosphorimager* available from Amersham Biosciences, Piscataway, N.J.

Where radionuclide labeling of DNA or RNA probes is not practical, the random-primer method can be used to incorporate an analogue, for example, the dTTP analogue 5-(N—(N- biotinyl-epsilon-aminocaproyl-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given gene product can be produced from the nucleic acid sequences.

The relative number of gene transcripts in cells can also be determined by reverse transcription of gene transcripts, followed by amplification of the reverse-transcribed transcripts by polymerase chain reaction (RT-PCR). The levels of gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). The methods for quantitative RT-PCR and variations thereof are within the skill in the art.

In some instances, it may be desirable to simultaneously determine the expression level of a plurality of different gene products in a sample. In other instances, it may be desirable to determine the expression level of the transcripts of all known genes correlated with a cancer. Assessing cancer-specific expression levels for hundreds of genes is time consuming and requires a large amount of total RNA (at least 20 µg for each Northern blot) and autoradiographic techniques that require radioactive isotopes.

To overcome these limitations, an oligolibrary, in microchip format (i.e., a microarray), may be constructed containing a set of probe oligodeoxynucleotides that are specific for a set of genes or gene products. Using such a micro array, the expression level of multiple microRNAs in a biological sample can be determined by reverse transcribing the RNAs to generate a set of target oligodeoxynucleotides, and hybridizing them to probe oligodeoxynucleotides on the microarray to generate a hybridization, or expression, profile. The hybridization profile of the test sample can then be compared to that of a control sample to determine which microRNAs have an altered expression level in ALL. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "specific probe oligonucleotide" or "probe oligonucleotide specific for a gene product" is meant a probe oligonucleotide that has a sequence selected to hybridize to a specific gene product, or to a reverse transcript of the specific gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal cells may be distinguished from ALL cells, and within ALL cells, different prognosis states (good or poor long term survival prospects, for example) may be determined. By comparing expression profiles of ALL cells in different states, information regarding which genes are important (including both up- and down-regulation of genes) in each of these states is obtained. The identification of sequences that are differentially expressed in ALL cells or normal cells, as well as differential expression resulting in different prognostic outcomes, allows the use of this information in a number of ways. For example, a particular treatment regime may be evaluated (e.g., to determine whether a chemotherapeutic drug act to improve the long-term prognosis in a particular patient). Similarly, diagnosis may be done or confirmed by comparing patient samples with the known expression profiles. Furthermore, these gene expression profiles (or individual genes) allow screening of drug candidates that suppress the ALL expression profile or convert a poor prognosis profile to a better prognosis profile.

Accordingly, the invention provides methods of diagnosing whether a subject has, or is at risk for developing, ALL, comprising reverse transcribing RNA from a test sample obtained from the subject to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample, wherein an alteration in the signal of at least one miRNA is indicative of the subject either having, or being at risk for developing, ALL.

The invention also provides methods of diagnosing a ALL associated with one or more prognostic markers, comprising measuring the level of at least one gene product in a ALL test sample from a subject and comparing the level of the at least one gene product in the ALL test sample to the level of a corresponding gene product in a control sample. An alteration (e.g., an increase, a decrease) in the signal of at least one gene product in the test sample relative to the control sample is indicative of the subject either having, or being at risk for developing, ALL associated with the one or more prognostic markers.

The ALL can be associated with one or more prognostic markers or features, including, a marker associated with an adverse (i.e., negative) prognosis, or a marker associated with a good (i.e., positive) prognosis. In certain embodiments, the ALL that is diagnosed using the methods described herein is associated with one or more adverse prognostic features.

Particular microRNAs whose expression is altered in ALL cells associated with each of these prognostic markers are described herein. In one embodiment, the level of the at least one gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more gene products in cells can result in the deregulation of one or more intended targets for these gene products, which can lead to the formation of ALL. Therefore, altering the level of the gene product (e.g., by decreasing the level of a gene product that is up-regulated in ALL cells, by increasing the level of a gene product that is down-regulated in cancer cells) may successfully treat the ALL. Examples of putative gene targets for gene products that are deregulated in ALL cells are described herein.

Accordingly, the present invention encompasses methods of treating ALL in a subject, wherein at least one gene product is de-regulated (e.g., down-regulated, up-regulated) in the cancer cells of the subject. When the at least one isolated gene product is down-regulated in the ALL cells, the method comprises administering an effective amount of the at least one isolated gene product such that proliferation of cancer cells in the subject is inhibited. When the at least one isolated gene product is up-regulated in the cancer cells, the method comprises administering to the subject an effective amount of at least one compound for inhibiting expression of the at least one gene, referred to herein as gene expression inhibition compounds, such that proliferation of ALL cells is inhibited.

The terms "treat", "treating" and "treatment", as used herein, refer to ameliorating symptoms associated with a disease or condition, for example, ALL, including preventing or delaying the onset of the disease symptoms, and/or lessening the severity or frequency of symptoms of the disease or condition. The terms "subject" and "individual" are defined herein to include animals, such as mammals, including but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated gene product is an amount sufficient to inhibit proliferation of a cancer cell in a subject suffering from ALL. One skilled in the art can readily determine an effective amount of a gene product to be administered to a given subject, by taking into account factors, such as the size and weight of the subject; the extent of disease penetration; the age, health and sex of the subject; the route of administration; and whether the administration is regional or systemic.

For example, an effective amount of an isolated gene product can be based on the approximate or estimated body weight of a subject to be treated. Preferably, such effective amounts are administered parenterally or enterally, as described herein. For example, an effective amount of the isolated gene product is administered to a subject can range from about 5 3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated gene product to a given subject. For example, a gene product can be administered to the subject once (e.g., as a single injection or deposition). Alternatively, a gene product can be administered once or twice daily to a subject for a period of from about three to about twenty-eight days, more particularly from about seven to about ten days. In a particular dosage regimen, a gene product is administered once a day for seven days. Where a dosage regimen comprises multiple administrations, it is understood that the effective amount of the gene product administered to the subject can comprise the total amount of gene product administered over the entire dosage regimen.

As used herein, an "isolated" gene product is one which is synthesized, or altered or removed from the natural state through human intervention. For example, a synthetic gene product, or a gene product partially or completely separated from the coexisting materials of its natural state, is considered to be "isolated." An isolated gene product can exist in substantially-purified form, or can exist in a cell into which the gene product has been delivered. Thus, a gene product which is deliberately delivered to, or expressed in, a cell is considered an "isolated" gene product. A gene product produced inside a cell from a precursor molecule is also considered to be "isolated" molecule.

Isolated gene products can be obtained using a number of standard techniques. For example, the gene products can be chemically synthesized or recombinantly produced using methods known in the art. In one embodiment, gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the gene products in cancer cells.

The gene products that are expressed from recombinant plasmids can be isolated from cultured cell expression systems by standard techniques. The gene products which are expressed from recombinant plasmids can also be delivered to, and expressed directly in, the cancer cells. The use of recombinant plasmids to deliver the gene products to cancer cells is discussed in more detail below.

The gene products can be expressed from a separate recombinant plasmid, or they can be expressed from the same recombinant plasmid. In one embodiment, the gene products are expressed as RNA precursor molecules from a single plasmid, and the precursor molecules are processed into the functional gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which are incorporated herein by reference) and the *E. coli* RNAse III system (e.g., as described in U.S. Published Patent Application No. 2004/0014113 to Yang et al., the entire disclosure of which are incorporated herein by reference).

Selection of plasmids suitable for expressing the gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol*, 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the gene products comprises a sequence encoding a precursor RNA under the control of the CMV intermediate-early promoter. As used herein, "under the control" of a promoter means that the nucleic acid sequences encoding the gene product are located 3' of the promoter, so that the promoter can initiate transcription of the gene product coding sequences.

The gene products can also be expressed from recombinant viral vectors. It is contemplated that the gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the gene products to cancer cells is discussed in more detail below.

The recombinant viral vectors of the invention comprise sequences encoding the gene products and any suitable promoter for expressing the RNA sequences. Suitable promoters include, for example, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the gene products in a cancer cell.

Any viral vector capable of accepting the coding sequences for the gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therap.* 2:301-310; Eglitis (1988), *Biotechniques* 6:608-614; Miller (1990), *Hum. Gene Therap.* 1:5-14; and Anderson (1998), *Nature* 392:25-30, the entire disclosures of which are incorporated herein by reference.

In certain embodiments, suitable viral vectors are those derived from AV and AAV. A suitable AV vector for expressing the gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the gene products, methods for constructing the recombinant AAV vector, and methods for delivering the vectors into target cells are described in Samulski et al. (1987), *J. Virol.* 61:3096-3101; Fisher et al. (1996), *J. Virol.*, 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference.

In a certain embodiment, a recombinant AAV viral vector of the invention comprises a nucleic acid sequence encoding a precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the sequences from the vector, the polyT termination signals act to terminate transcription.

In other embodiments of the treatment methods of the invention, an effective amount of at least one compound which inhibits expression can also be administered to the subject. As used herein, "inhibiting gene expression" means that the production of the active, mature form of gene product after treatment is less than the amount produced prior to treatment. One skilled in the art can readily determine whether expression has been inhibited in a cancer cell, using for example the techniques for determining transcript level discussed above for the diagnostic method. Inhibition can occur at the level of gene expression (i.e., by inhibiting transcription of a gene encoding the gene product) or at the level of processing (e.g., by inhibiting processing of a precursor into a mature, active gene product).

As used herein, an "effective amount" of a compound that inhibits expression is an amount sufficient to inhibit proliferation of a cancer cell in a subject suffering from a cancer associated with a cancer-associated chromosomal feature. One skilled in the art can readily determine an effective amount of an expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate or estimated body weight of a subject to be treated. Such effective amounts are administered parenterally or enterally, among others, as described herein. For example, an effective amount of the expression-inhibiting compound administered to a subject can range from about 5-3000 micrograms/kg of body weight, from about 700-1000 micrograms/kg of body weight, or it can be greater than about 1000 micrograms/kg of body weight.

One skilled in the art can also readily determine an appropriate dosage regimen for administering a compound that inhibits expression to a given subject. For example, an expression-inhibiting compound can be administered to the subject once (e.g., as a single injection or deposition). Alternatively, an expression-inhibiting compound can be administered once or twice daily to a subject for a period of from about three to about twenty-eight days, more preferably from about seven to about ten days. In a particular dosage regimen, an expression-inhibiting compound is administered once a day for seven days. Where a dosage regimen comprises multiple administrations, it is understood that the effective amount of the expression-inhibiting compound administered to the subject can comprise the total amount of compound administered over the entire dosage regimen.

Suitable compounds for inhibiting expression include double-stranded RNA (such as short- or small-interfering RNA or "siRNA"), antisense nucleic acids, and enzymatic RNA molecules, such as ribozymes. Each of these compounds can be targeted to a given gene product and destroy or induce the destruction of the target gene product.

For example, expression of a given gene can be inhibited by inducing RNA interference of the gene with an isolated double-stranded RNA ("dsRNA") molecule which has at least 90%, for example at least 95%, at least 98%, at least 99% or 100%, sequence homology with at least a portion of the gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target gene product.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of which are incorporated herein by reference.

Expression of a given gene can also be inhibited by an antisense nucleic acid. As used herein, an "antisense nucleic acid" refers to a nucleic acid molecule that binds to target RNA by means of RNA-RNA or RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, PNA) that generally comprise a nucleic acid sequence complementary to a contiguous nucleic acid sequence in a gene product. The antisense nucleic acid can comprise a nucleic acid sequence that is 50-100% complementary, 75-100% complementary, or 95-100% complementary to a contiguous nucleic acid sequence in a gene product. Nucleic acid sequences for the gene products are provided herein. Without wishing to be bound by any theory, it is believed that the antisense nucleic acids activate RNase H or another cellular nuclease that digests the gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given gene can also be inhibited by an enzymatic nucleic acid. As used herein, an "enzymatic nucleic acid" refers to a nucleic acid comprising a substrate binding region that has complementarity to a contiguous nucleic acid sequence of a gene product, and which is able to specifically cleave the gene product. The enzymatic nucleic acid substrate binding region can be, for example, 50-100% complementary, 75-100% complementary, or 95-100% complementary to a contiguous nucleic acid sequence in a gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated gene products. Exemplary methods for producing and testing dsRNA or siRNA molecules are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one gene product, or at least one compound for inhibiting expression, will inhibit the proliferation of cancer cells in a subject who has a cancer associated with a cancer-associated chromosomal feature. As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the gene products or gene expression-inhibiting compounds. An inhibition of cancer cell proliferation can also be inferred if the absolute number of such cells increases, but the rate of tumor growth decreases.

The number of cancer cells in a subject's body can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The gene products or gene expression-inhibiting compounds can be administered to a subject by any means suitable for delivering these compounds to cancer cells of the subject. For example, the gene products or expression inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one gene product or gene expression inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy)propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A gene product or gene expression inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and intravenous administration into the patient.

In the present methods, a gene product or gene product expression inhibiting compound can be administered to the subject either as naked RNA, in combination with a delivery reagent, or as a nucleic acid (e.g., a recombinant plasmid or viral vector) comprising sequences that express the gene product or expression inhibiting compound. Suitable delivery reagents include, e.g., the Mirus Transit TKO lipophilic reagent; lipofectin; lipofectamine; cellfectin; polycations (e.g., polylysine), and liposomes.

Recombinant plasmids and viral vectors comprising sequences that express the gene products or gene expression inhibiting compounds, and techniques for delivering such plasmids and vectors to cancer cells, are discussed herein.

In a particular embodiment, liposomes are used to deliver a gene product or gene expression-inhibiting compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands which bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH₃ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the gene products or gene expression inhibition compounds (or nucleic acids comprising sequences encoding them) to tumor cells.

The gene products or gene expression inhibition compounds can be formulated as pharmaceutical compositions, sometimes called "medicaments," prior to administering them to a subject, according to techniques known in the art. Accordingly, the invention encompasses pharmaceutical compositions for treating ALL. In one embodiment, the pharmaceutical compositions comprise at least one isolated gene product and a pharmaceutically-acceptable carrier. In a particular embodiment, the at least one gene product corresponds to a gene product that has a decreased level of expression in ALL cells relative to suitable control cells.

In other embodiments, the pharmaceutical compositions of the invention comprise at least one expression inhibition compound. In a particular embodiment, the at least one gene expression inhibition compound is specific for a gene whose expression is greater in ALL cells than control cells.

Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is incorporated herein by reference.

The present pharmaceutical formulations comprise at least one gene product or gene expression inhibition compound (or at least one nucleic acid comprising sequences encoding them) (e.g., 0.1 to 90% by weight), or a physiologically acceptable salt thereof, mixed with a pharmaceutically-acceptable carrier. The pharmaceutical formulations of the invention can also comprise at least one gene product or gene expression inhibition compound (or at least one nucleic acid comprising sequences encoding them) which are encapsulated by liposomes and a pharmaceutically-acceptable carrier.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one gene product or gene expression inhibition compound (or at least one nucleic acid comprising sequences encoding them) which is resistant to degradation by nucleases. One skilled in the art can readily synthesize nucleic acids which are nuclease resistant, for example by incorporating one or more ribonucleotides that are modified at the 2'-position into the gene products. Suitable 2'-modified ribonucleotides include those modified at the 2'-position with fluoro, amino, alkyl, alkoxy, and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one gene product or gene expression inhibition compound (or at least one nucleic acid comprising sequences encoding them). A pharmaceutical composition for aerosol (inhalational) administration can comprise 0.01-20% by weight, preferably 1%-10% by weight, of the at least one gene product or gene expression inhibition compound (or at least one nucleic acid comprising sequences encoding them) encapsulated in a liposome as described above, and a propellant. A carrier can also be included as desired; e.g., lecithin for intranasal delivery.

The invention also encompasses methods of identifying an anti-ALL agent, comprising providing a test agent to a cell and measuring the level of at least one gene product in the cell. In one embodiment, the method comprises providing a test agent to a cell and measuring the level of at least one gene product associated with decreased expression levels in ALL cells. An increase in the level of the gene product in the cell, relative to a suitable control cell, is indicative of the test agent being an anti-ALL agent.

In other embodiments the method comprises providing a test agent to a cell and measuring the level of at least one gene product associated with increased expression levels in ALL cells. A decrease in the level of the gene product in the cell, relative to a suitable control cell, is indicative of the test agent being an anti-ALL agent.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one gene product (e.g., Northern blotting, in situ hybridization, RT-PCR, expression profiling) are also well known in the art.

DEFINITIONS

The term "array" is used interchangeably with the term "microarray" herein.

The term "cancer," as used herein, refers to the physiological condition in mammals that is typically characterized by unregulated cell proliferation, and the ability of those cells to invade other tissues.

The term "expression," as used herein, refers to the conversion of the DNA sequence information into messenger RNA (mRNA) or protein. Expression may be monitored by measuring the levels of full-length mRNA, mRNA fragments, full-length protein, or protein fragments.

The term "fusion protein" is intended to describe at least two polypeptides, typically from different sources, which are operably linked. With regard to polypeptides, the term operably linked is intended to mean that the two polypeptides are connected in a manner such that each polypeptide can serve its intended function. Typically, the two polypeptides are covalently attached through peptide bonds. The fusion protein is preferably produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame).

The phrase "gene expression signature," as used herein refers to the unique pattern of gene expression in a cell, and in particular, a cancer cell.

The term "hybridization," as used herein, refers to the process of binding, annealing, or base-pairing between two single-stranded nucleic acids. The "stringency of hybridization" is determined by the conditions of temperature and ionic strength. Nucleic acid hybrid stability is expressed as the melting temperature or Tm, which is the temperature at which the hybrid is 50% denatured under defined conditions. Equations have been derived to estimate the Tm of a given hybrid; the equations take into account the G+C content of the nucleic acid, the length of the hybridization probe, etc. (e.g., Sambrook et al., 1989). To maximize the rate of annealing of the probe with its target, hybridizations are generally carried out in solutions of high ionic strength (6×SSC or 6×SSPE) at a temperature that is about 20-25° C. below the Tm. If the sequences to be hybridized are not identical, then the hybridization temperature is reduced 1-1.5° C. for every 1% of mismatch. In general, the washing conditions should be as stringent as possible (i.e., low ionic strength at a temperature about 12-20° C. below the calculated Tm). As an example, highly stringent conditions typically involve hybridizing at 68° C. in 6×SSC/5×Denhardt's solution/1.0% SDS and washing in 0.2×SSC/0.1% SDS at 65° C. The optimal hybridization conditions generally differ between hybridizations performed in solution and hybridizations using immobilized nucleic acids. One skilled in the art will appreciate which parameters to manipulate to optimize hybridization.

The term "nucleic acid," as used herein, refers to sequences of linked nucleotides. The nucleotides may be deoxyribonucleotides or ribonucleotides, they may be standard or non-standard nucleotides; they may be modified or derivatized nucleotides; they may be synthetic analogs. The nucleotides may be linked by phosphodiester bonds or non-hydrolyzable bonds. The nucleic acid may comprise a few nucleotides (i.e., oligonucleotide), or it may comprise many nucleotides (i.e., polynucleotide). The nucleic acid may be single-stranded or double-stranded.

The term "prognosis," as used herein refers to the probable course and outcome of a cancer, and in particular, the likelihood of recovery.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

REFERENCES

The patents, publications and other materials used herein to illuminate the invention or provide additional details respecting the practice of the invention, are incorporated by reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

1. Pasquale E B (2005) Nat Rev Mol Cell Biol 6:462-475.
2. Easty D J, Hill S P, Hsu M Y, Fallowfield M E, Florenes V A, Herlyn M, Bennett D C (1999) Int J Cancer 84:494-501.
3. Vogt T, Stolz W, Welsh J, Jung B, Kerbel R S, Kobayashi H, Landthaler M, McClelland M (1998) Clin Cancer Res 4:791-797.
4. Lugli A, Spichtin H, Maurer R, Mirlacher M, Kiefer J, Huusko P, Azorsa D, Terracciano L, Sauter G, Kallioniemi O P, Mousses S, Tornillo L (2005) Clin Cancer Res 11:6450-6458.
5. Wu Q, Suo Z, Risberg B, Karlsson M G, Villman K, Nesland J M (2004) Pathol Oncol Res 10:26-33.
6. Walker-Daniels J, Coffman K, Azimi M, Rhim J S, Bostwick D G, Snyder P, Kerns B J, Waters D J, Kinch M S (1999) Prostate 41:275-280.
7. Zelinski D P, Zantek N D, Stewart J C, Irizarry A R, Kinch M S (2001) Cancer Res 61:2301-2306.
8. Miyazaki T, Kato H, Fukuchi M, Nakajima M, Kuwano H (2003) Int J Cancer 103:657-663.
9. Kitties R A, Baffoe-Bonnie A B, Moses T Y, Robbins C M, Ahaghotu C, Huusko P, Pettaway C, Vijayakumar S, Bennett J, Hoke G, et al. (2006) J Med Genet 43:507-511.
10. Oba S M, Wang Y J, Song J P, Li Z Y, Kobayashi K, Tsugane S, Hamada G S, Tanaka M, Sugimura H (2001) Cancer Lett 164:97-104.
11. Gu Y, Nakamura T, Alder H, Prasad R, Canaani O, Cimino G, Croce C M, Canaani E (1992) Cell 71:701-708.
12. Johansson B, Moorman A V, Haas O A, Watmore A E, Cheung K L, Swanton S, Secker-Walker L M (1998) European 11q23 Workshop participants. Leukemia 12:779-787.
13. Aasheim H C, Terstappen L W, Logtenberg T (1997) Blood 90:3613-3622.
14. Nakamura T, Canaani E, Croce C M (2007) Proc Natl Acad Sci USA in press.
15. Thomas M, Gessner A, Vornlocher H P, Hadwiger P, Greil J, Heidenreich O (2005) Blood 106:3559-3566.
16. Zeisig B R, Milne T, Garcia-Cuellar M-P, Schreiner S, Martin m-E, Fuchs U, Borkhardt A, Chanda S K, Walker J, Soden R, et al. (2004) Mol Cell Biol 24:617-628.

17. Yu C, Subler M, Rahmani M, Reese E, Krystal G, Conard D, Dent P, Grant S (2003) Cancer Biol. Therapy 2:544-551.
18. Rubinfeld H, Serger R (2005) Mol Biotech 31:151-174.
19. Fox T, Coll J T, Xie X, Ford P J, Germann U A, Porter M D, Pazhanisamy S, Fleming M A, Galullo V, Su M S, Wilson K P (1998) Protein Sci 11:2249-2255.
20. Armstrong S A, Staunton J E, Silverman L B, Pieters R, den Boer M L, Minden M D, Sallan S E, Lander E S, Golub T R, Korsmeyer S J (2002) Nat Genet 30:41-47.
21. Rozovskaia T, Ravid-Amir O, Tillib S, Getz G, Feinstein E, Agrawal H, Nagler A, Rappaport E F, Issaeva I, Matsuo Y, et al. (2003) Proc Natl Acad Sci USA 100:7853-7858.
22. Xu C, Robbins D, Frost J, Dang A, Lange-Carter C, Cobb M H (1995) Proc Natl Acad Sci USA 92:6808-6812.
23. Grammer T C, Blenis J (1977) Oncogene 14:1635-1642.
24. Janis L S, Cassidy R M, Kromer L F (1999) J Neurosci 19:4962-4971.

What is claimed is:

1. A method to interfere with an acute lymphoblastic leukemia (ALL) response signaling pathway in at least one leukemic cell producing an ALL1/AF9 chimeric fusion protein, wherein the method comprises:
   administering, to at least one leukemic cell, an ALL1/AF9-specific siRNA which suppresses expression of an ALL1/AF9 chimeric fusion protein, thereby interfering with an acute lymphoblastic leukemia (ALL) response signaling pathway; and,
   administering at least one EphA7-specific siRNA.

2. The method of claim 1, wherein the at least one leukemic cell further comprises a living organism.

3. The method of claim 2, wherein the organism is a human.

4. The method of claim 1, wherein the at least one leukemic cell is selected from the group consisting of: a K562 leukemic cell transfected with an ALL1/AF9 chimeric fusion protein construct; a pro-B leukemic SEMK2 cell having a t(9; 11) chromosome translocation; and a pro-B leukemic RS4 cell having a t(9; 11) chromosome translocation.

5. A method to interfere with an acute lymphoblastic leukemia (ALL) response signaling pathway in at least one leukemic cell producing an ALL1/AF9 chimeric fusion protein, wherein the method comprises:
   administering, to at least one leukemic cell, an ALL1/AF9-specific siRNA which suppresses expression of an ALL1/AF9 chimeric fusion protein, thereby interfering with an acute lymphoblastic leukemia (ALL) response signaling pathway; and,
   administering 5-iodotubercidin to the leukemic cell.

6. The method of claim 1, wherein the ALL1/AF9-specific siRNA is a SEMj siRNA.

7. A method of inducing apoptosis in, and/or suppressing growth of, at least one leukemic cell producing an ALL1/AF4 chimeric fusion protein, wherein the method comprises:
   suppressing expression of an ALL1/AF4 chimeric fusion protein in the leukemic cell by treating the leukemic cell with an ALL1/AF4-specific siRNA; and
   suppressing expression of EphA7 in the leukemic cell by treating the leukemic cell with an EphA7-specific siRNA.

8. The method of claim 7, further comprising: inhibiting Erk1/2 phosphorylation in the leukemic cell by treating the leukemic cell with 5-iodotubercidin.

9. The method of claim 7, wherein the ALL1/AF4-specific siRNA is an SEMj siRNA.

10. The method of claim 7, wherein the EphA7-specific siRNA is an siEphA7#1 siRNA.

11. The method of claim 7, wherein the EphA7-specific siRNA is an siEphA7#2 siRNA.

12. The method of claim 7, wherein at least two EphA7-specific siRNA target EphA7 mRNA at two distinct regions.

13. The method of claim 5, wherein the at least one leukemia cell further comprises a living organism.

14. The method of claim 13, wherein the living organism is a human.

15. The method of claim 5, wherein the at least one leukemic cell is selected from the group consisting of: a K562 leukemic cell transfected with an ALL1/AF9 chimeric fusion protein construct; a pro-B leukemic SEMK2 cell having a t(9; 11) chromosome translocation; and a pro-B leukemic RS4 cell having a t(9; 11) chromosome translocation.

16. The method of claim 1, wherein the ALL1/AF9-specific siRNA is a SEMj siRNA.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaagggagt gggaaaggaa                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttccgagctc atcgaagtct                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caatagcgcc tcatctgaca                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atgcagcgaa atggaaaact                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tagtacctca ggcgggtcac                                                  20
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttgtcgttgg acgttcacat                                              20
```